(12) United States Patent
Neuenschwander

(10) Patent No.: US 8,821,460 B1
(45) Date of Patent: Sep. 2, 2014

(54) ANTI-CHANNELING STOOL MANAGEMENT SYSTEM

(76) Inventor: Lois Jean Neuenschwander, Oneco, FL (US)

( * ) Notice: Subject to any disclaimer, the term of this patent is extended or adjusted under 35 U.S.C. 154(b) by 107 days.

(21) Appl. No.: 13/422,783

(22) Filed: Mar. 16, 2012

(51) Int. Cl.
*A61M 1/00* (2006.01)

(52) U.S. Cl.
USPC .......................................................... 604/319

(58) Field of Classification Search
USPC .......................................................... 604/319
See application file for complete search history.

(56) References Cited

U.S. PATENT DOCUMENTS

| | | | | |
|---|---|---|---|---|
| 2,529,999 A * | 11/1950 | Chambers | ...................... | 604/347 |
| 3,103,930 A * | 9/1963 | Collett et al. | .................. | 604/355 |
| 3,522,807 A * | 8/1970 | Millenbach | .................... | 604/355 |
| 3,734,096 A * | 5/1973 | Millenbach | .................... | 604/355 |
| 4,784,656 A * | 11/1988 | Christian | ....................... | 604/355 |
| 4,834,737 A * | 5/1989 | Khan | ........................ | 604/385.14 |
| 5,421,827 A * | 6/1995 | Temple | .......................... | 604/355 |
| 5,741,239 A * | 4/1998 | Mulholland | ................... | 604/328 |
| 6,355,022 B1 * | 3/2002 | Osborn et al. | ............ | 604/385.17 |
| 6,432,096 B1 * | 8/2002 | McFall et al. | ............ | 604/385.17 |
| 6,635,799 B1 * | 10/2003 | Osborn et al. | ................ | 604/367 |
| 7,537,587 B2 * | 5/2009 | Carstens | .................. | 604/385.22 |
| 7,727,218 B2 * | 6/2010 | Lavon et al. | ................... | 604/395 |
| 7,763,003 B1 * | 7/2010 | Yip | ........................... | 604/385.19 |
| 7,766,887 B2 * | 8/2010 | Burns et al. | ............... | 604/385.14 |
| 7,771,406 B2 * | 8/2010 | Mueller et al. | ........... | 604/385.19 |
| 7,772,455 B1 * | 8/2010 | Roe et al. | ........................ | 604/360 |
| 7,867,211 B2 * | 1/2011 | Carstens | .................. | 604/385.22 |
| 8,062,277 B2 * | 11/2011 | Fleming | .................... | 604/385.17 |
| 8,382,734 B1 * | 2/2013 | Neuenschwander | ..... | 604/385.19 |
| 2003/0120178 A1 * | 6/2003 | Heki | ............................ | 600/574 |
| 2006/0264883 A1 * | 11/2006 | Carstens | ....................... | 604/396 |
| 2006/0264885 A1 * | 11/2006 | Carstens | ....................... | 604/396 |
| 2007/0142816 A1 * | 6/2007 | Carstens | ....................... | 604/396 |
| 2007/0255239 A1 * | 11/2007 | Hataya | .......................... | 604/319 |
| 2010/0274209 A1 * | 10/2010 | Roe et al. | ...................... | 604/378 |

* cited by examiner

*Primary Examiner* — Susan Su
*Assistant Examiner* — Guy K Townsend
(74) *Attorney, Agent, or Firm* — Dorothy S. Morse

(57) ABSTRACT

A stool management and collection system for acutely and chronically ill patients that prevents channeling which can quickly lead to the breakdown of patient skin, patient discomfort, and the spread of disease. Although several preferred embodiments are disclosed herein, each has an absorbent insert ring component with a waterproof interior that alone or in combination with other structure directs stool into an associated stool collection bag. Super absorbent polymer (SAP) resin may also employed as a part of the stool containment system structure. In addition, the system's stool collection bag isn't positioned on the patient's backside as in the prior art, instead being secured in approximately the same area where an incontinence pad is normally positioned, so that diarrhea is contained from start to finish.

20 Claims, 24 Drawing Sheets

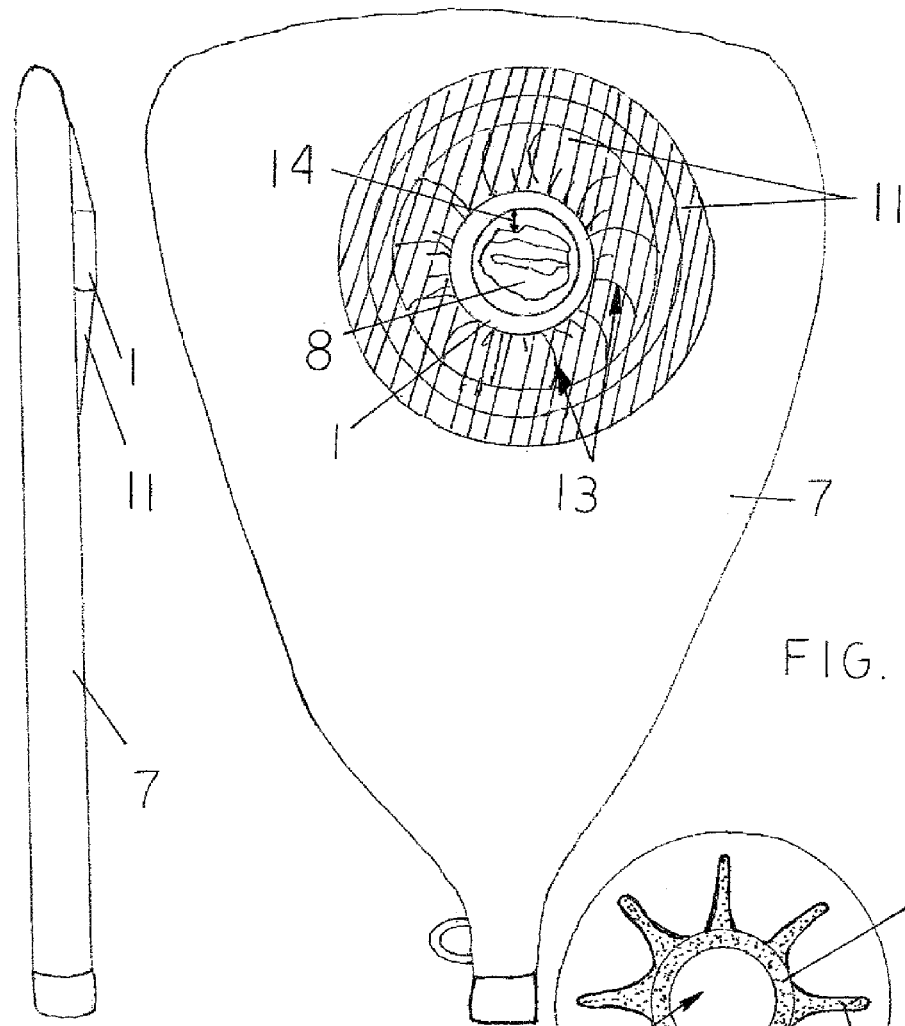
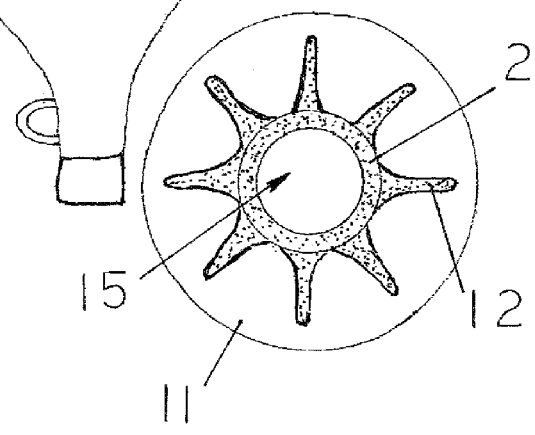

ANTI-CHANNELING STOOL MANAGEMENT SYSTEM

CROSS REFERENCES TO RELATED APPLICATIONS

This invention relates in part to aspects of another U.S. patent application previously filed by the same applicant herein, which was entitled "Adult Diaper System" and filed on Jan. 8, 2010 with a patent application Ser. No. 12/655,853. Both facilitate stool management and secure a stool collection container to patient's skin. In addition, both can optionally employ hook-and-loop fasteners and both incorporate a free-zone around the bandage opening in an attempt to prevent channeling. Also, both inventions tackle the issue of incorrect positioning of the stool containing device on the buttocks that is common to prior art devices. Furthermore, both of these inventions offer an option to avoid the indignity of a standard diaper that catches stool next to a patient's skin, which can lead to its breakdown. Thus, as a result of the common structure in both inventions, the inventor herein respectfully requests that domestic priority be granted for the current patent application herein based upon the inventor's previously-filed patent application identified hereinabove for an "Adult Diaper System".

BACKGROUND

1. Field of the Invention

The present invention is in the field of devices used for incontinence management, and since it has structure that is free of the flaws commonly found in prior art incontinence management devices, the present invention both facilitates stool management and prevents the spread of disease that would otherwise be prevalent with discharge of infectious stool (such as c-diff, etc.) into a diaper. The flaws and disadvantages which have been consistently associated with prior art devices in the field of incontinence management are: 1) skin breakdown under the bandage component (known as channeling), and channeling requires a discontinuation of use of the device until the skin is healed; 2) devices becoming torn off while non-comatose patients move about in their beds, which often occurs and results in skin tears that can also require discontinuation of the device until the skin is healed; 3) lodging of semi-formed stool in the prior art devices, making them unusable and requires a discontinued use of the device even when infectious semi-formed stool is present; 4) a decrease in patient dignity and comfort when stool is deposited into a diaper; and 5) excoriation of patient skin and even more severe skin breakdown when the device is discontinued. Although several preferred embodiments are disclosed herein, the most preferred embodiments each have an absorbent insert ring component. (or equivalent) and an absorbent insert extension that alone or in combination with other structure directs stool into an associated stool collection bag (which can be configured to envelop the patient in the same manner as a diaper). Super Absorbent Polymer (hereinafter SAP) resin may also used as a part of the stool containment structure of the present invention, or non-toxic, non-irritating, non-corrosive, and super absorbent materials capable of absorbing forty-to-sixty times their weight in fluid (instead of the cellulose or other fiber-based products that only absorb approximately twenty times their weight in fluid). In addition, a stool collection bag used as a part of the present invention is typically secured in approximately the same area where an incontinence pad would be positioned to facilitate passage of formed stool, so that diarrhea can be contained from start to finish. For example, one preferred embodiment of the present invention employs at least one portion of a hook-and-loop fastener attached to its stool collection bag for help in securing an absorbent insert ring component against the area of the patient immediately around the anus (also hereinafter referred to as 'rectal opening'). The absorbent insert ring component, in combination with any absorbent insert extension used therewith, prevent channeling. A preferred embodiment structured for female patients also employs at least one portion of a hook-and-loop fastener to secure the female outer flesh protrusion (the vulva-flaps) to a diaper in a manner that directs urine into the diaper and away from the patient's skin, while a preferred embodiment structured for male patients has a convenient lined opening that allows urine to be directed into a diaper as a collection bag where urine storage is away from patient skin. When waterproof seals are used as a part of the present invention, any diaper used with it is converted into a plastic stool and urine collection bag, sealing off urine, stool, and any associated odor that would otherwise be released from the bag. In this embodiment, the hook and loop portions of a hook-and-loop type of fastener are also connected together to provide structure that protects the wearer's body from contact with urine or stool. As a result, the diaper used as a part of the present invention is adapted to become a leak-proof, odor-proof, and waterproof collection bag.

2. Description of Related Art

The present invention is configured to reduce the spread of disease-bearing organisms in patients with diarrhea, and the breakdown of patient skin experienced in extended or repeat contact with liquid stool, by blocking channeling, which results from the leakage of liquid stool under bandages placed in close association with rectal opening to secure a prior art stool collection bag. *Clostrium difficile* (also referred to herein as *C. difficile* or c-diff) is a commonly-known bacterium that is currently being spread at alarming rates during patient care in U.S. hospitals and long-term care facilities, largely as a result of the overuse of certain antibiotics. Worldwide problems with c-diff infections also occur. *C. difficile* can cause diarrhea, as well as life-threatening inflammation or perforation of the colon. It is also a spore-releasing bacterium, and is resistant to some antibiotics. Alcohol-based hand sanitizers do not kill the dormant *C. difficile* spores, nor does hand washing with soap and water. In addition, special bleach cleansers are required to stop the spread of infection once *C. difficile* spores come into contact with other surfaces where they can survive for weeks or months. Also, once spores come into contact with hospital uniforms, bed linens, and diapers, the spores can travel widely throughout a hospital or long-term care facility, as only a long soaking in bleach will kill them. The number of c-cliff infections has increased significantly during the last 20-30 years due to the incomplete containment of diarrhea run-off, and recently became a leading healthcare-associated infection, surpassing the number of infections due to methicillin-resistant Staphylococcus aureus (MRSA).

Dealing with the cleanup of diarrhea in hospital and long-term care facilities is always time-consuming and expensive (often exceeding $4,000 per patient in hospital-acquired *C. difficile*) and has traditionally included diapers, creams, ointments, skin breakdown fixes such as sterile bandages and medications, and sufficient labor to keep the patient clean so that skin healing can occur. Prior art stool collection devices are currently allowed to stay in place for a maximum time period of only twenty-four hours, and they are removed more frequently should stool leakage occur, as repeat or extended contact with liquid stool quickly causes skin breakdown. Also, the channeling of diarrhea under a bandage that holds a stool collector in place and subsequent breakdown of patient skin, leads to subsequent discontinuation of the stool collection device, resulting in the increased opportunity for spread of c-diff infection to others. Annual diaper cost for one hundred patients with diarrhea is estimated at more than $200,000, and the annual cost of creams for one hundred diarrhea patients may add another $20,000. Staff labor costs for those same one hundred patients may approach $1 million, with disposal cost for used diapers estimated at approximately $32,000. Thus, the estimated cost of treating one hundred diarrhea patients is approximately $1.25 million per year. It is estimated that on any given day in U.S. hospitals more than 7,000 patients have a c-diff infection, leading to more than 500,000 people infected in U.S. hospitals with *C. difficile* annually. Thus, the treatment costs of hospital-acquired or nursing home-onset of diarrhea in the U.S. as a result of c-diff infection is now estimated to be approximately a $3-6 billion annual expense. It is also estimated that one-third of patients with a *C. difficile* diagnosis return to a hospital with a recurrence of the disease. Since the present invention prevents channeling (that leads to skin break and discontinuation of prior art stool collection devices), use of the present invention would break the chain of infection and slow down or stop the current C. difficile epidemic (which cause approximately 32,000 deaths in the United States each year), and would also significantly reduce the high cost currently experienced by hospitals and long-term care facilities for the treatment of c-diff infections. In addition, if a patient gets a hospital-acquired c-diff infection, the hospital then becomes responsible for the cost of hospital care for the remainder of the patient's stay. In addition, if the patient has a recurrence of c-diff, on the patient's return, the hospital is also responsible for the cost/expenses for the return visit.

Another difficulty in the use of prior art stool collectors (which is overcome by present invention use), is that its positioning is on the backside of a patient in bed, and when a patient slides down, the bandage adhering the stool collector to the patient's skin pulls off, often tearing the skin. Another deficiency in prior art stool collectors, is that as a patient with serious diarrhea heals, the diarrhea gradually turns into a formed stool which can get stuck in the opening of a stool collector, making prior art stool collectors dysfunctional and necessitating their removal from the patient for the remainder of the patient's recovery. The present invention offers solutions that overcome all of these deficiencies. No invention is known that has the same features as the present invention, its same structure, or provides the same benefits and advantages to a user as the present invention.

BRIEF SUMMARY OF THE INVENTION

The primary objective of this invention is to provide a medical device that overcomes the flaws of prior art stool collection devices and methods. Another objective of this invention is to provide a medical device that diminishes the spread of c-diff and other infectious diseases present in human stool. It is also an objective of this invention to provide a medical device for stool management that lessens the breakdown of patient skin. A further objective of this invention is to bring advances into low-tech, hands-on patient care that has had much fewer changes over the years than high-tech medical instruments and devices. It is a further objective of this invention to provide a medical device that lowers the labor involved in hands-on care of patients, particularly those with skin breakdown. A further objective of this invention is to change medical practice by lowering the cost of labor and materials used per patient. It is also an objective of this invention to provide a medical device that prevents the loss of patient dignity.

The present invention is a stool management and collection system for acutely and chronically ill patients that prevents channeling which can quickly lead to the breakdown of patient skin, patient discomfort, and the spread of disease. Since patients are so varied in size, it is contemplated for the present invention to be produced in multiple sizes, such as small, medium, and large, although not limited thereto, to make certain channeling does not occur. Although several preferred embodiments are disclosed herein, each has an absorbent insert ring component with a waterproof interior that alone or in combination with other structure (such as a bandage and seal) directs stool into an associated stool collection bag. The inner diameter of the ring component used on a patient should leave a minimum distance of approximately three-sixteenths of an inch around a rectal opening for the application of barrier cream or other sealing substance. Super absorbent polymer (SAP) resin is a preferred part of the ring component, providing a core that can absorb approximately 40% to 60% of its weight in fluid. However, other material with similar absorbency could also be used as part of the ring component's core as long it had no toxic, irritating, or corrosive properties that might adversely affect the condition of patient skin, in addition, the present invention can be used with prior art stool collection bags, or newly developed bags that overcome some of the deficiencies known in prior art stool collection bags. Furthermore, the present system's stool collection bag isn't positioned on the patient's backside as in the prior art, instead being secured in approximately the same area where an incontinence pad is normally positioned, so that diarrhea is contained from start to finish, even in the final stages of patient recovery when it is semi-solid. Nine preferred embodiments are disclosed herein, however, the present invention should not be considered as limited thereto, and one should consult the appended claims for a determination of the structure and scope of the present invention.

BRIEF DESCRIPTION OF THE SEVERAL VIEWS OF THE DRAWINGS

FIG. 6 is a side view of a first preferred embodiment of the present invention with two absorbent inserts connected to the prior art stool collection bag shown in FIG. 5, the absorbent insert ring component shown in FIG. 1 and the absorbent insert extension shown in FIG. 8 below.

FIG. 7 is a perspective view from the top of the first preferred embodiment of the present invention with the two absorbent inserts connected to the prior art stool collection bag shown in FIG. 5, the absorbent insert ring component shown in FIG. 1 and the absorbent insert extension shown in FIG. 8 below, the absorbent insert extension positioned to be in fluid communication with the ring component and having a loose construction with folds that provide a capability for expansion as moisture and soft stool are drawn away from a user's skin, the absorbent insert extension having elongated projections made from absorbent material such as SAP, with FIG. 7 also showing a slightly expanded rectal opening (typical of a patient with diarrhea) that is aligned with the central bore of the absorbent insert ring component and the aperture of the absorbent insert extension.

FIG. 8 is a sectional view of a preferred absorbent insert extension that is usable as a part of the first preferred embodiment of the anti-channeling stool management system of the present invention, with the absorbent insert extension having a circular circumference, a central aperture, a core of SAP around the aperture, and multiple elongated projections radially-extending from the core that are made from absorbent material that draws moisture away from the core and a patient's skin.

Figure 1:
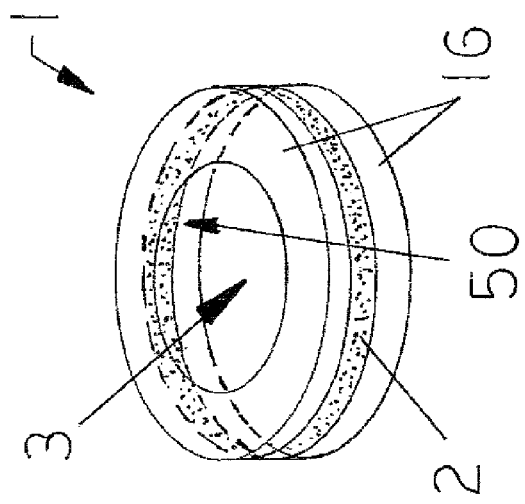
FIG. 1 is a perspective view of an absorbent insert ring component usable as a part of the most preferred embodiments of the anti-channeling stool management systems of the present invention, with the absorbent insert ring component shown having a central bore, a waterproof interior, and a core made from absorbent material, such as SAP, that is encased within an absorbent exterior layer/cover.

| COMPONENT LIST | |
|---|---|
| 1 | Absorbent insert ring component |
| 2. | Absorbent core (preferably made from SAP material) |
| 3. | Bore through ring component 1 |
| 4. | Bandage |
| 5. | Hole in bandage 4 |
| 6. | Seal (provides waterproof connection between ring component 1 and bandage 4) |
| 7. | Prior art stool collection bag |
| 8. | Rectal opening (enlarged due to stool incontinence) |
| 9. | Bag opening (through which stool from a patient enters collection bag 7) |
| 10. | Drain (opening through which stool exits collection bag 7 or collection bag 17) |
| 11, 11', 11'', 11''' | Absorbent insert extension (can be different sizes and shapes) |
| 12. | Elongated projections depending outwardly from absorbent core 2 |
| 13. | Expansion folds in absorbent insert extension 11 |
| 14. | Stool containment gap between rectal opening 8 and ring component 1 (provides space for barrier creams, ointments, and/or other aids that direct stool into collection bag 7 or 17A) |
| 15. | Aperture in absorbent insert extension 11 (becomes aligned with bore 3 through ring component 1) |
| 16. | Absorbent exterior covering for absorbent insert extension 11 (made from material that is non-irritating to human skin) |
| 17A. | Top member of the two-part stool collection bag |
| 17B. | Bottom member of the two-part stool collection bag |
| 18. | Stool slide |
| 19. | Snap/wing |
| 20. | Snap |
| 21. | Rough/hook portion of a hook-and-loop fastener (may have varying perimeter configurations, including straight, arcuate, Y-shaped, but not limited thereto) |
| 22. | Widened butterfly-shaped bandage |
| 23. | Non-collapsible small soft beads (preferably Styrofoam, prevents bottom member 17B of the two-part stool collection bag from collapsing during stool collection activity) |
| 24. | Fluid communication means between the top member 17A and the bottom member 17B of the two-part stool collection bag (can be an anti-reflux valve) |
| 25. | Angled bore through ring component 1 |
| 26. | Y-shaped fastener (adhesive or a rough/hook portion of a hook-and-loop fastener) |
| 27A. | Female patient |
| 27B. | Male patient |
| 28. | Vaginal area of female patient 27A |
| 29. | Arcuate bandage (is connected in part between rectal area 8 and vaginal area 28) |
| 30. | Estimated stool contamination area of patient 27A (area where skin breakdown of patient is greatest) |
| 31. | Soft/loop portion of a hook-and-loop fastener (also could be adhesive) |
| 32. | Single collection bag for stool and urine |
| 33. | Underwear |
| 34. | Sling (configured for alignment with vaginal area 28) |
| 35. | Wearable stool and urine collection bag |
| 36. | Stool transfer opening |
| 37. | Urine transfer opening |
| 38. | Bed (or other patient support) |
| 39. | Tubing |
| 40. | Foley catheter bag |

COMPONENT LIST

| | |
|---|---|
| 41. | Non-adhesive side of bandage 4 |
| 42. | Human naval |
| 43. | Target area for adhesive/bonding material on bandage, absorbent insert extension, or stool collection bag |
| 44. | Fastening tab on wearable stool and urine collection bag 35 |
| 45. | Wing supporting tabs 44 on wearable stool and urine collection bag 35 |
| 46. | Adhesive material (bonds stool slide to upper interior portion of stool collection bag) |
| 47. | Reinforced edge around stool transfer opening 36 in wearable stool/urine collection bag 35 |
| 48. | Reinforced edge around urine transfer opening 37 in wearable stool/urine collection bag 35 |
| 49. | Break-away portion of arcuate bandage 29 |
| 50. | Waterproof interior wall of absorbent insert ring component 1 |
| 51. | Deodorizer means (optional) |

DETAILED DESCRIPTION OF THE INVENTION

Figure 20:
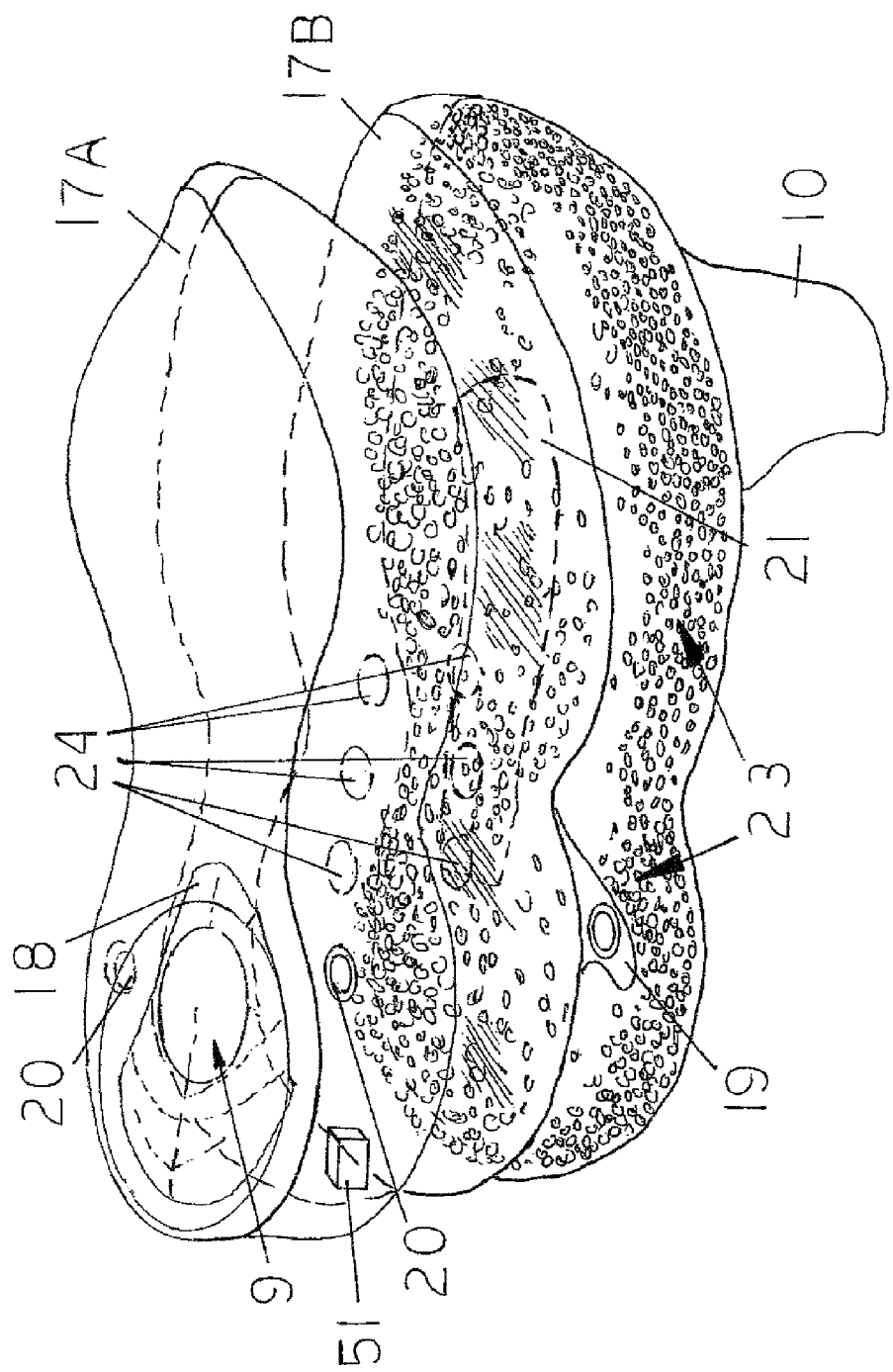
FIG. 20 is a perspective view from the side of a two-part stool collection bag usable as a part of various preferred embodiments of the present invention, with the bottom bag member having snap/wing connectors for pulling up the bottom bag member and maintaining it in an open configuration for stool transfer, sufficient small beads in the lower bag to maintain an open configuration therein for stool collection, optional deodorizer means, and one-way valve means for fluid communication from the upper bag member downward into the lower bag member.
Figure 21:
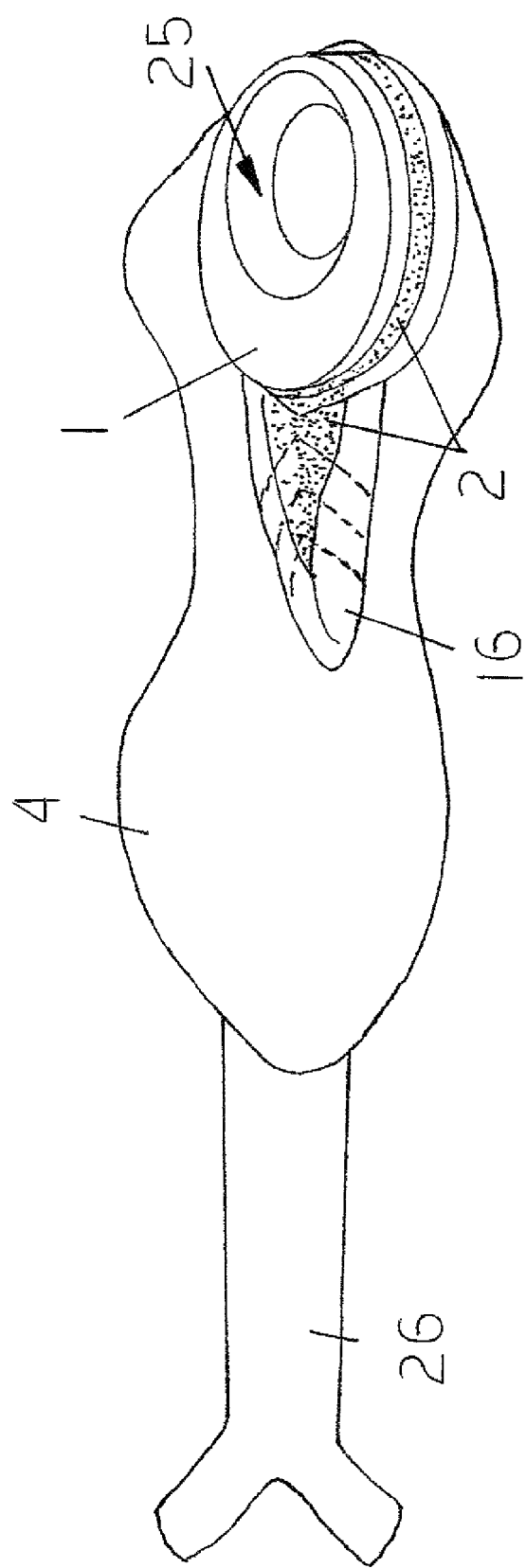
FIG. 21 is a perspective view of a sixth preferred embodiment of the present invention absorbent insert ring component, absorbent insert extension, and elongated bandage, with the absorbent insert ring component having a downwardly tapering bore and the bandage having a Y-shaped fastener made from the soft/loop portion of a hook-and-loop fastener or adhesive material secured to it on the end of the bandage remote from the ring component.
Figure 22:
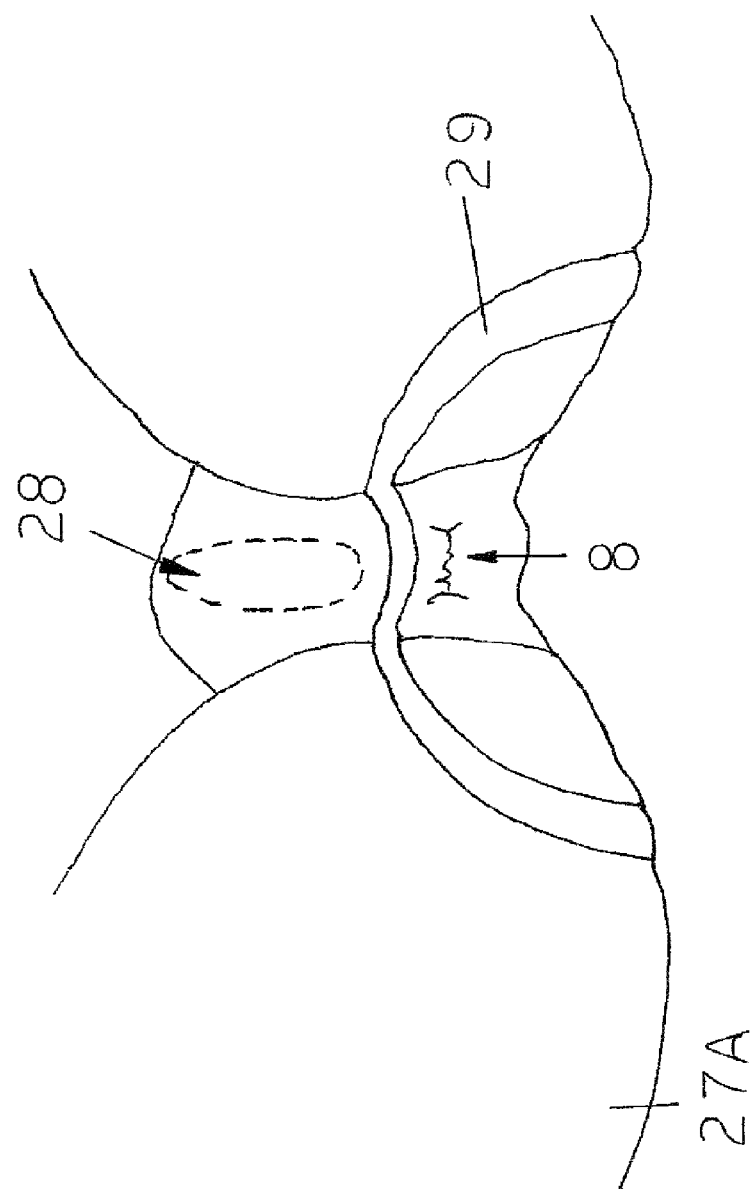
FIG. 22 is a top view of an arcuate bandage that is usable as a part of a seventh preferred embodiment of the present invention, with the visible portion of the arcuate bandage extending across the center part of the crotch area of a female patient between the rectal and vaginal areas, and further extending outwardly onto both sides of the buttocks area of the patient.
Figure 23:
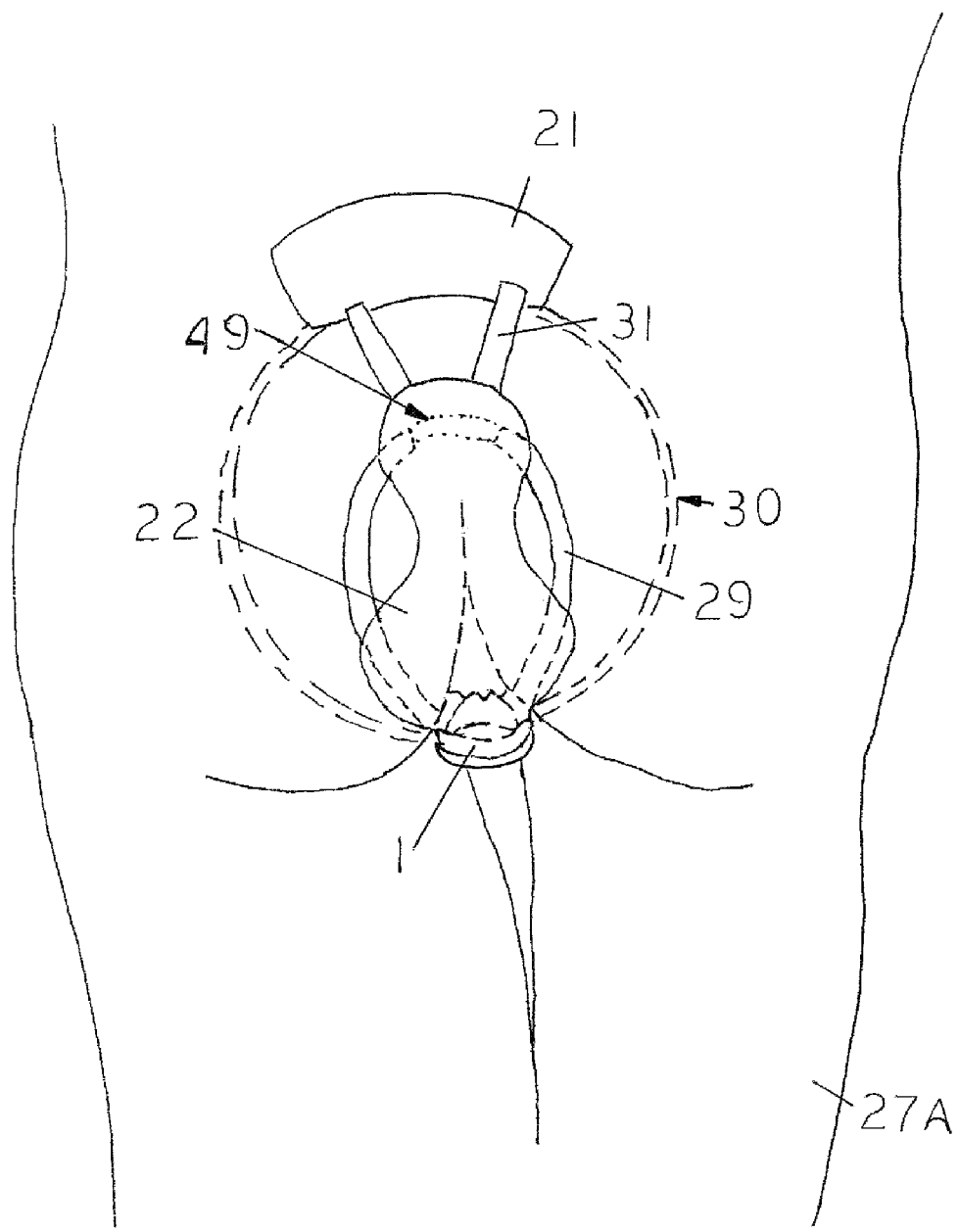
FIG. 23 is a rear view of the seventh preferred embodiment of the present invention which has the arcuate bandage extending from the center part of the crotch area of a female patient and then upwardly onto the patient's buttocks, and a generally butterfly-shaped bandage having an attached absorbent insert ring component aligned with the rectal opening of the patient and extending upwardly across the back of the patient for connection outside the zone of potential stool influence that is likely to experience skin breakdown should stool leakage occur for any reason.
Figure 24:
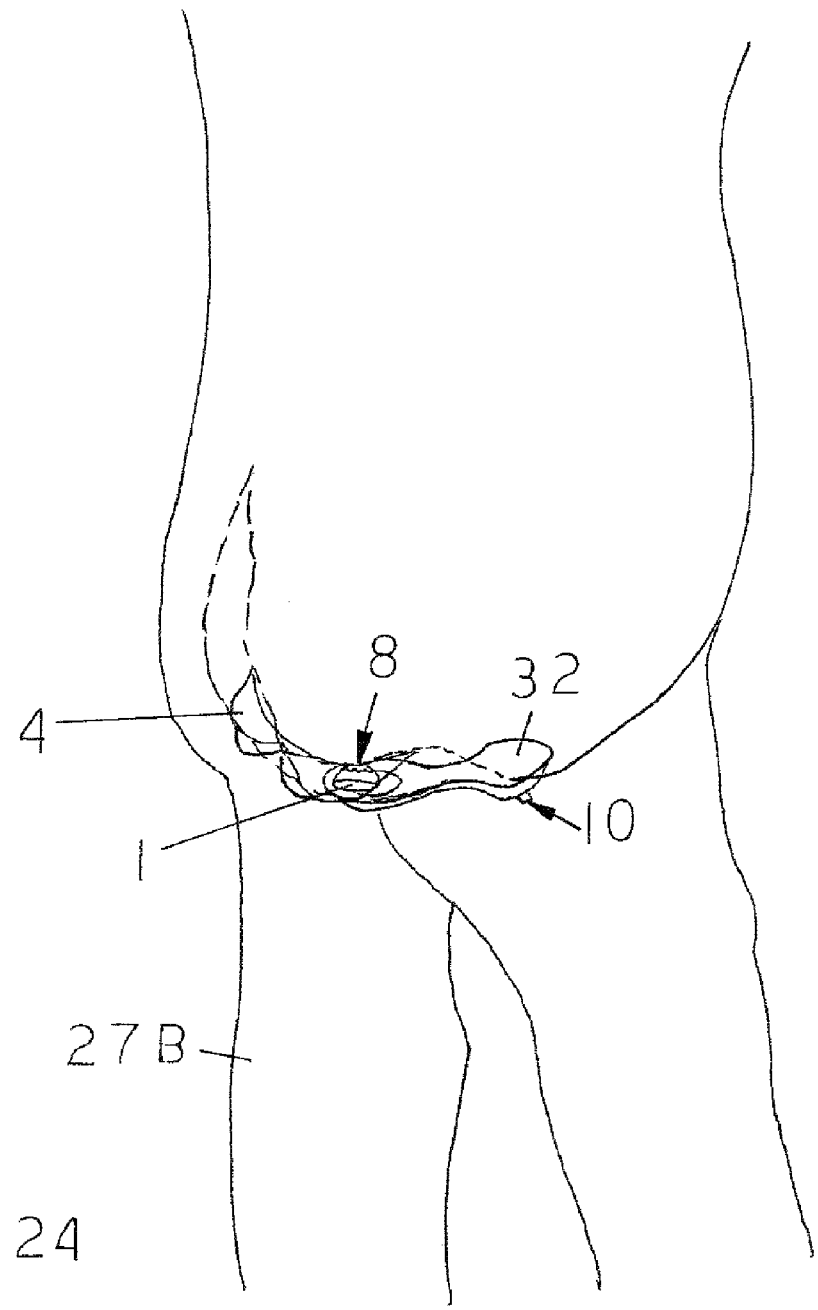
FIG. 24 is a rear view of a male patient showing that it is intended for preferred embodiments of the present invention to be positioned for use in approximately the same area where an incontinence pad would be used, the vertical orientation of the illustration selected to better provide understanding of the intended positioning without implying that the patient is ambulatory.
Figure 25:
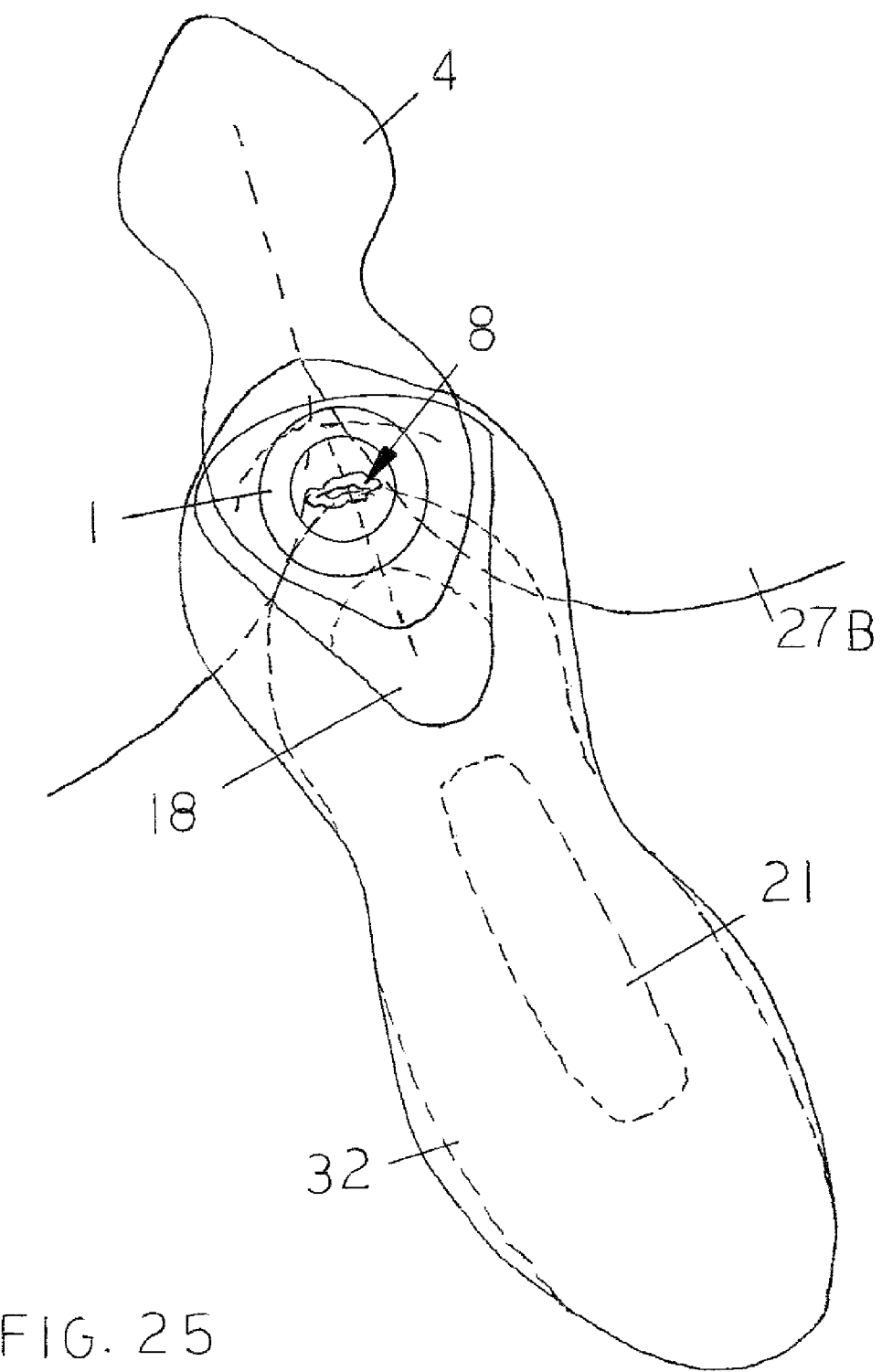
FIG. 25 is a top view of an eighth preferred embodiment of the present invention contemplated for use on a male patient for stool collection, with an adhesive bandage extending rearwardly from the rectal opening for attachment to the backside of a patient and a stool and urine collection bag extending forwardly from the rectal opening, with a rough/hook portion of a hook-and-loop fastener attached to the bottom surface of the collection bag that securely fixes the collection bag to an adjacent part of a male patient's undergarment.
Figure 26:
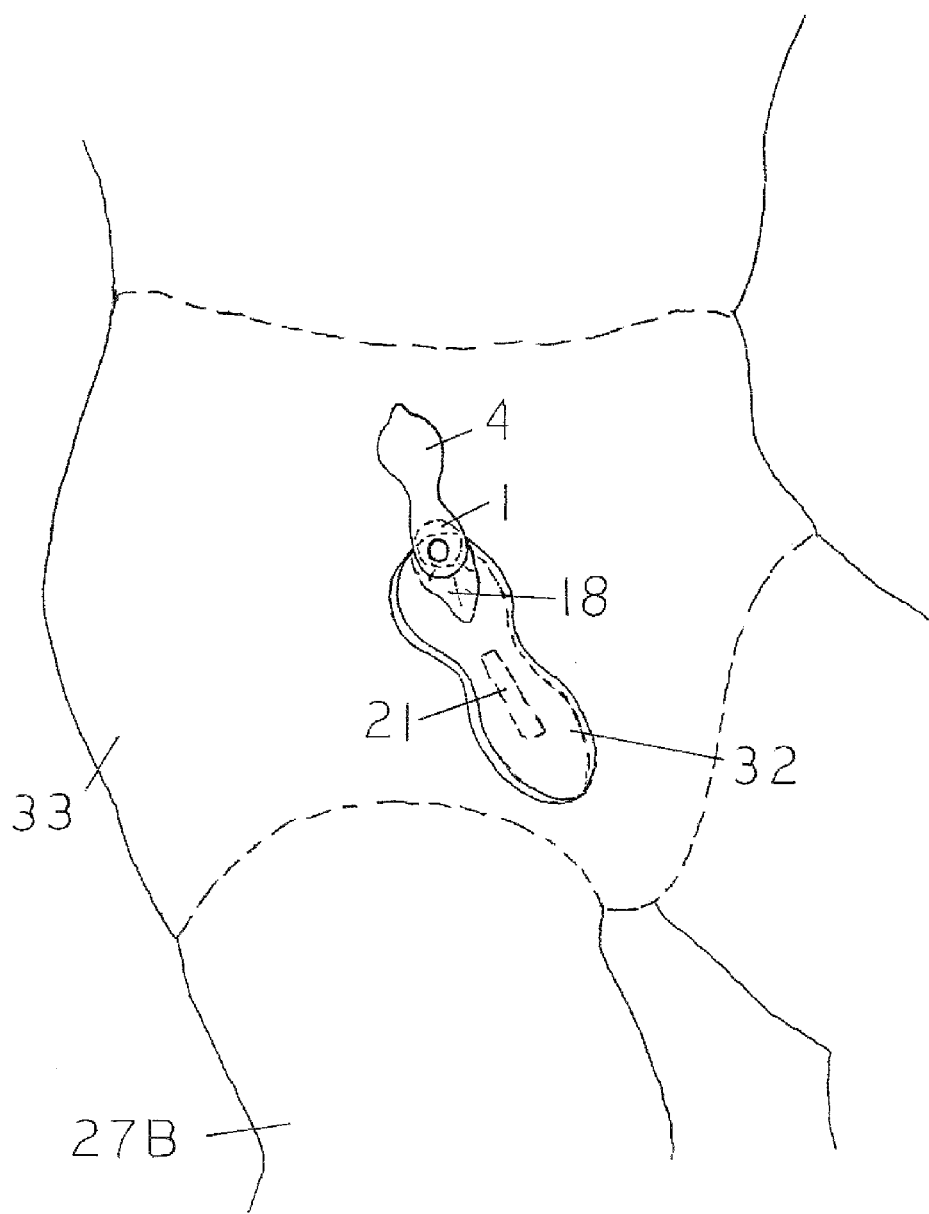
FIG. 26 is a perspective view of the eighth preferred embodiment of the present invention in its intended position of use.

The present invention is a stool management and collection system for acutely and chronically ill patients 27 that prevents channeling which can quickly lead to the breakdown of patient skin, patient discomfort, and the spread of disease. Although several preferred embodiments are disclosed herein, each has an absorbent insert ring component 1 with a waterproof interior 50 that alone or in combination with other structure directs stool into an associated stool collection bag (such as 7, 17, 32, or other). Super absorbent polymer (SAP) resin may also employed as an absorbent core 2 in the present invention stool containment system structure. In addition, the system's stool collection bag (7, 17, 32, or other) isn't positioned on the patient's backside as in the prior art, instead being secured in approximately the same area where an incontinence pad is normally positioned, so that diarrhea (not shown) is contained from start to finish. Although nine preferred embodiments are specifically disclosed herein, the present invention should not be considered as limited thereto, and one should consult the appended claims for a determination of the structure and scope of the present invention. FIGS. 1-4 disclose the absorbent insert ring component 1 usable as a part of preferred embodiments of the present invention to prevent channeling of diarrhea under a bandage (4, 22, or other) which leads to skin breakdown and an opportunity for spread of disease. FIGS. 5-11 disclose a prior art stool collection bag 7 and two preferred embodiments of the present invention that can be used with prior art bag 7. FIGS. 12-15 disclose a fourth preferred embodiment of the present invention having a two-part stool collection bag (17A and 17B), while FIGS. 16-19 disclose a fifth preferred embodiment that is a variation of the fourth preferred embodiment, having a widened butterfly-shaped bandage 22 and two absorbent insert extensions 11" and 11'". FIG. 20 shows a two-part stool collection bag (comprising 17A and 17B), with the bottom bag member 17B filled in part with soft beads that help prevent bottom bag member 17B from collapsing so that liquid stool is able to continually flow via gravity from top bag member 17A into the bottom bag member 17B. FIG. 21 discloses an optional way in which to secure the bandage 4 that holds the absorbent insert ring component 1 in place around a rectal opening 8. FIGS. 22 and 23 respectively disclose sixth and seventh preferred embodiments of the present invention comprising a portion of an arcuate bandage 29 that extends onto a patient's buttocks being secured in the crotch area between the vaginal area 28 of a female patient 27A and the rectal opening 8. FIGS. 24-26 disclose an eighth preferred embodiment of the present invention that is used for male patient 27B and includes a single stool and urine collection bag 32. In addition FIGS. 27-30 show a ninth preferred embodiment of the present invention for female patients 27A with accommodation for stool and urine collection, while FIG. 31 shows a male patient 27B in bed 38 with the drain 10 of a present invention stool management and collection system connected via tubing 39 to a Foley catheter bag 40 supported by the frame of bed 38.

Figure 4:
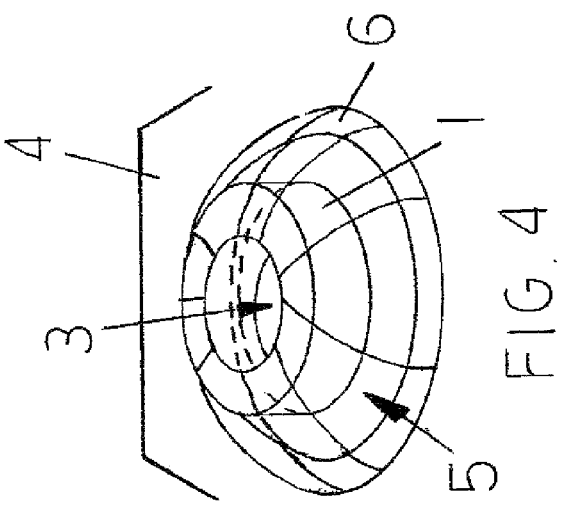
FIG. 4 is a perspective view from the top of a seal extending over the connection between an absorbent insert ring component and a bandage, while leaving central bore unblocked for transfer of stool therethrough, with the ring component configured and positioned to direct stool into a collection bag through its waterproof central bore while the seal helps to block passage of stool through any portion of the hole in the bandage (referred to as channeling) that would allow liquid stool to work its way under the bandage and quickly lead to the breakdown of patient skin around the patient's rectal opening and any other areas where stool would make contact with patient skin.
Figure 3:
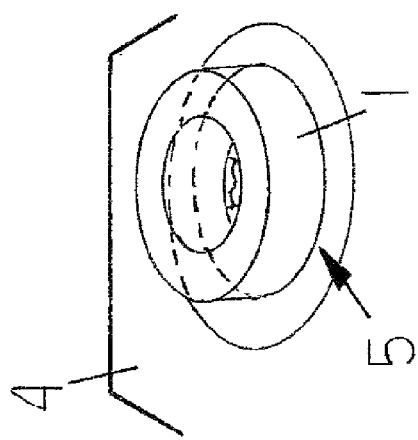
FIG. 3 is a perspective view from the top of the hole through the bandage having aligned positioning with the absorbent insert ring component in FIG. 1 that allows stool passage through the ring component's waterproof central bore.
Figure 2:
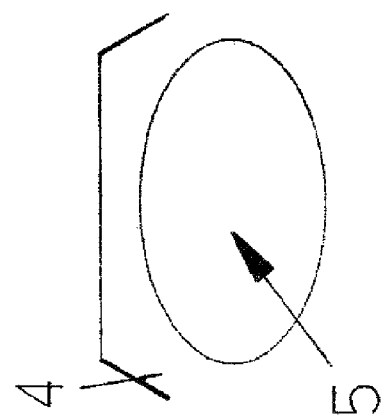
FIG. 2 is a perspective view from the top of a portion of a bandage with hole therethrough can be used with the absorbent insert ring component in FIG. 1 for alignment of both with a rectal opening for stool collection purposes.

FIGS. 1-4 show an absorbent insert ring component 1 usable as a part of the most preferred embodiments of the present invention anti-channeling stool management systems and its relation to a hole 5 in a bandage 4 and a seal 6. FIG. 1 is a perspective view of the absorbent insert ring component 1 having a central bore 3 and a core 2 made from absorbent material, such as SAP, that is encased within an absorbent exterior covering 16. Although not limited thereto, it is preferred for exterior covering 16 to be made from air-spun absorbent fiber. Also, although not shown, it is contemplated for barrier cream or other ointment to be used within bore 3 to further reduce the risk of channeling under a bandage 4. Also, as will be seen in other later illustrations of different embodiments of the present invention, bore 3 may not always be centered within ring component 1, particularly those embodiments used for female patients 27A. FIG. 2 is a perspective view from the top of a portion of bandage 4 with hole 5 therethrough, which can be employed to securely place and maintain ring component 1 in its preferred position of use for stool collection. FIG. 3 is a perspective view from the top of the hole 5 through bandage 4 having aligned positioning with ring component 1 that allows stool passage through the central bore 3 of ring component 1. FIG. 4 is a perspective view from the top of a seal 6 extending between ring component 1 and bandage 4 that directs stool through central bore 3 while concurrently blocking passage of stool through the hole 5 in bandage 4. The sizes of ring component 1 and bandage 4 will vary according to patient size (perhaps being produced in small, medium, and large sizes), and in its desired position of use will typically allow a minimum of approximately three-sixteenths-of-an-inch between its waterproof interior wall 50 and a rectal opening 8 (see FIG. 5) for the placement of barrier cream (not shown) or other substances intended to block the flow of liquid stool (not shown) away from rectal opening 8 where it could quickly cause a breakdown in patient skin. Although for clarity of illustration seal 6 is not always shown, in most preferred embodiments of the present invention seal 6 is included as a means of sealing the hole 5 in bandage 4 to direct all stool present through the central bore 3 of ring component 1.

Figure 5:
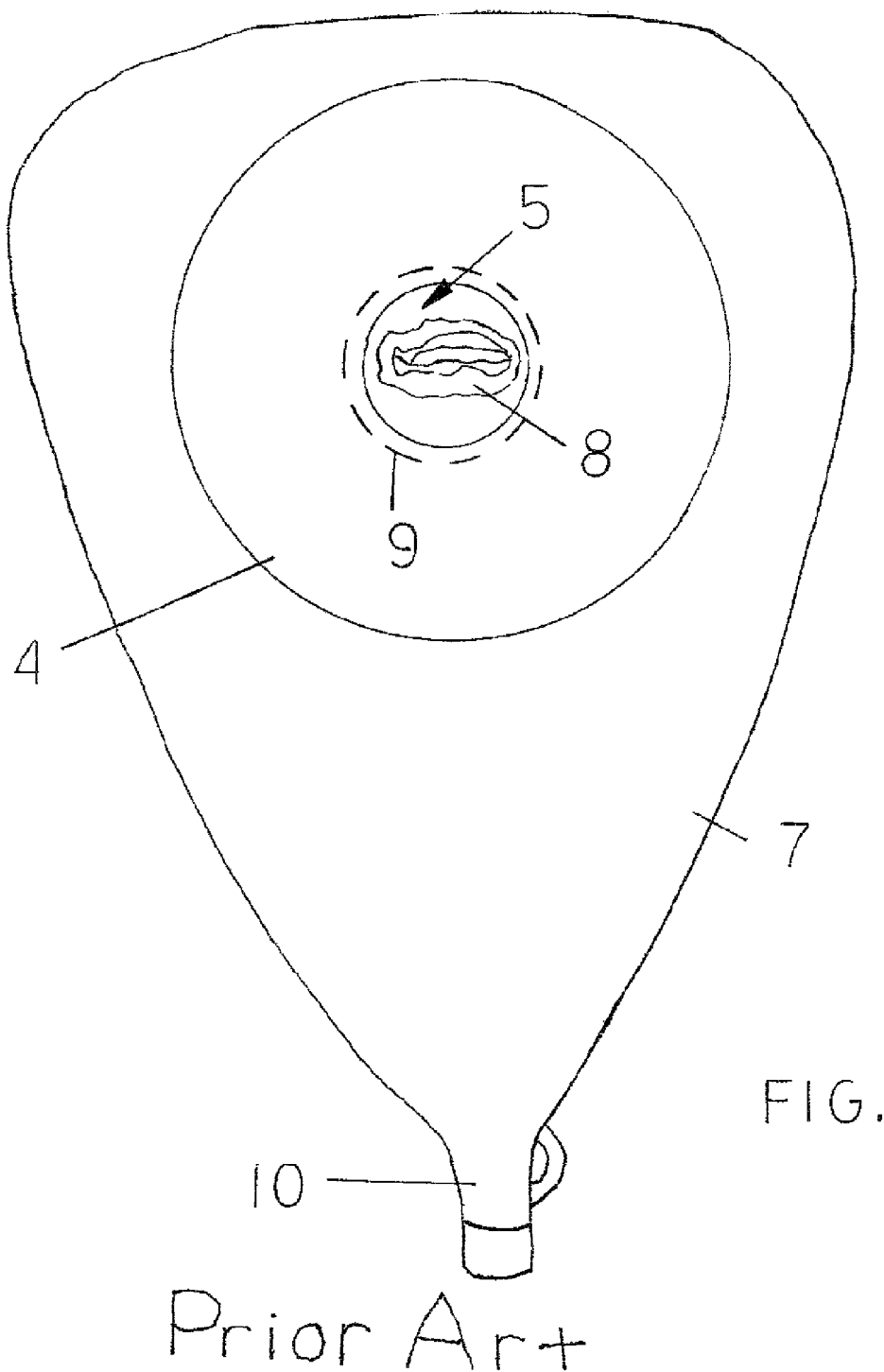
FIG. 5 is a top view of a prior art stool collection bag that can be with some preferred embodiments of present invention anti-channeling stool management system.
Figure 9:
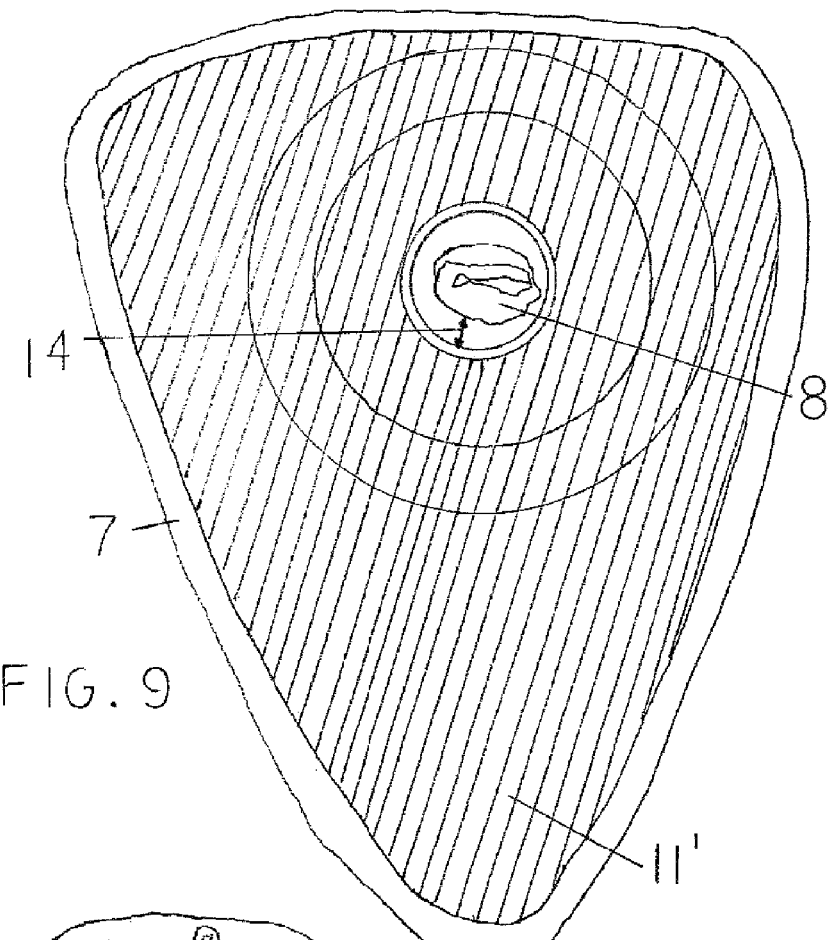
FIG. 9 is a front view of a second preferred embodiment of the present invention with a larger capacity absorbent insert extension than was shown in FIGS. 7 and 8, which is close in size and configuration to its associated stool collection bag so that the extension is able to provide more moisture wicking capability than can be provided in the first preferred embodiment of the present invention, with FIG. 9 also showing a slightly expanded rectal opening in alignment with the central bore of the absorbent insert ring component and the aperture of the absorbent insert extension.
Figure 10:
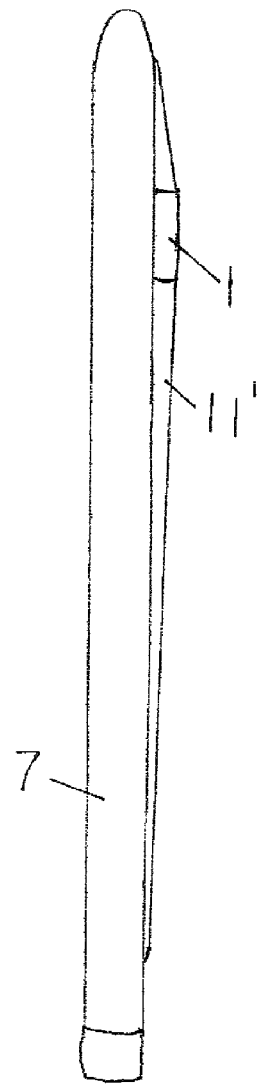
FIG. 10 is a side view of a second preferred absorbent insert extension that is usable as a part of the second preferred embodiment of the anti-channeling stool management system of the present invention, with the absorbent insert extension having a length dimension nearly as long as that of the associated stool collection bag.
Figure 11:
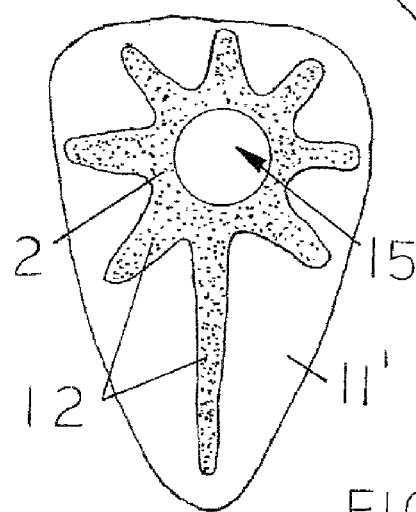
FIG. 11 is a cross-sectional view of the larger capacity absorbent insert extension having a generally shield-shaped circumference, a central aperture, and an internal core of SAP with multiple radially-extending elongated projections extending from the core into multiple directions for trapping fluid and soft stool and drawing it away from the central aperture and a patient's skin, which is usable as a part of the second preferred embodiment of the anti-channeling stool management system of the present invention.

FIGS. 5-11 show a prior art stool collection bag 7 and how it can be used with two preferred embodiments of the present invention. Although not shown, the prior art stool collection bag 7 and absorbent insert extensions 11 and 11' shown in FIGS. 5-11 are preferably secured to one another with glue, adhesive, and/or other bonding material. FIG. 5 is a top view of prior art stool collection bag 7, while FIG. 6 is a side view of a first preferred embodiment of the present invention with two absorbent inserts connected to it, the ring component 1 shown in FIG. 1 and the absorbent insert extension 11 shown in FIG. 8. FIG. 7 is a perspective view from the top of the first preferred embodiment of the present invention with the two absorbent inserts (ring component 1 and absorbent insert extension 11 connected to prior art stool collection bag 7, the absorbent insert extension 11 positioned to be in fluid communication with ring component 1 to draw moisture and soft stool away from rectal opening 8 and patient skin, with absorbent insert extension 11 also having a loose construction with folds 13 that provide a capability for expansion as moisture and soft stool are drawn away from a user's skin, the absorbent insert extension 11 further having elongated projections 12 made from absorbent material such as SAP, with FIG. 7 also showing a slightly expanded rectal opening 8 that is aligned with the central bore 3 of ring component 1 and the aperture 15 of absorbent insert extension 11. FIG. 8 is a sectional view of a first preferred embodiment of absorbent insert extension 11 that is usable as a part of the first preferred embodiment of the anti-channeling stool management system of the present invention, with the absorbent insert extension 11 having a circular circumference, a central aperture 15, a SAP core 2, and multiple elongated projections 12 made from absorbent material (such as SAP) that radially-extend from core 2 and draw moisture away from central aperture 15 and a patient's skin. FIG. 9 is a front view of a second preferred embodiment of the present invention with a larger capacity absorbent insert extension 11' than was shown in FIGS. 6-8, which is close in size and configuration to its associated stool collection bag 7 to provide more moisture wicking capability than is provided in the first preferred embodiment of the present invention (shown in FIGS. 6-8), with FIG. 9 also showing a slightly expanded rectal opening 8 in alignment with the central bore 3 of the absorbent insert ring component 1 and the aperture 15 of the absorbent insert extension 11'. FIG. 10 is a side view of the second preferred absorbent insert extension that is usable as a part of the second preferred embodiment of the anti-channeling stool management system of the present invention, with the absorbent insert extension 11' having a length dimension nearly as long as that of the associated stool collection bag 7. FIG. 11 is a cross-sectional view of the larger capacity absorbent insert extension 11' which is usable as a part of the second preferred embodiment of the anti-channeling stool management system of the present invention. Larger capacity absorbent insert extension 11' has an aperture 15 and a core 2 of SAP with multiple radially-extending elongated projections 12 extending from core 2 for use in trapping moisture and soft stool and drawing it away from aperture 15 and a patient's skin.

Figure 12:
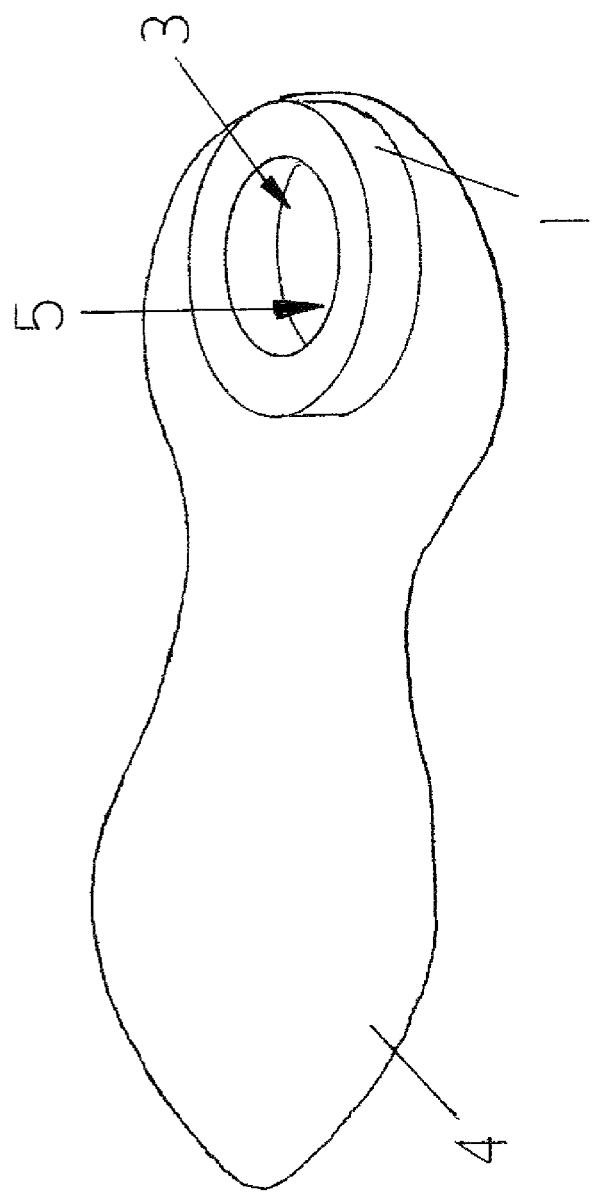
FIG. 12 is a perspective view of an absorbent insert ring component in a third preferred embodiment of the present invention associated with an elongated bandage used to assist in securing the ring component into its desired position of use.
Figure 13:
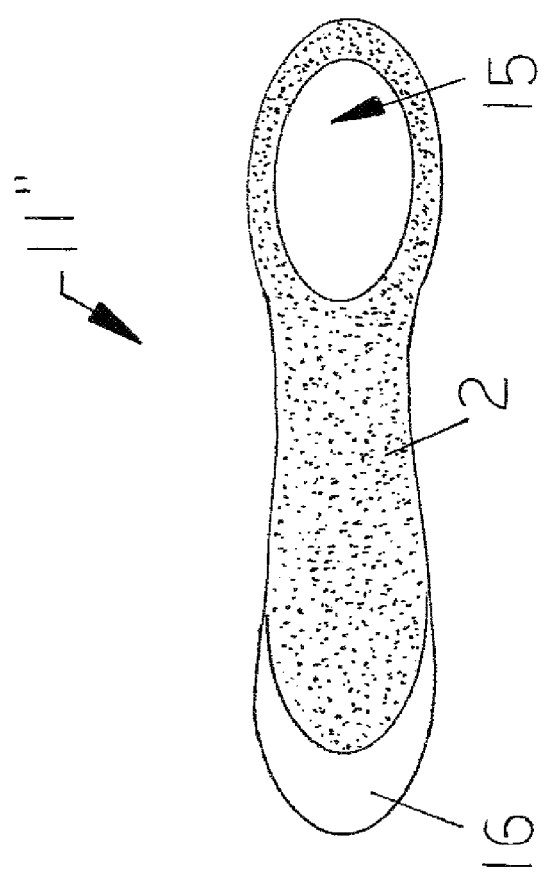
FIG. 13 is a top view of an elongated absorbent insert extension having an aperture near one of its ends and a core made from absorbent material, such as SAP, that can be used as a part of the third preferred embodiment of the present invention, with the absorbent exterior layer/cover only partially shown to reveal the presence of the SAP material throughout the extension's interior without the use of the elongated projections shown in FIGS. 8 and 11, however, during use the absorbent exterior layer/cover totally encases the SAP core material.
Figure 14:
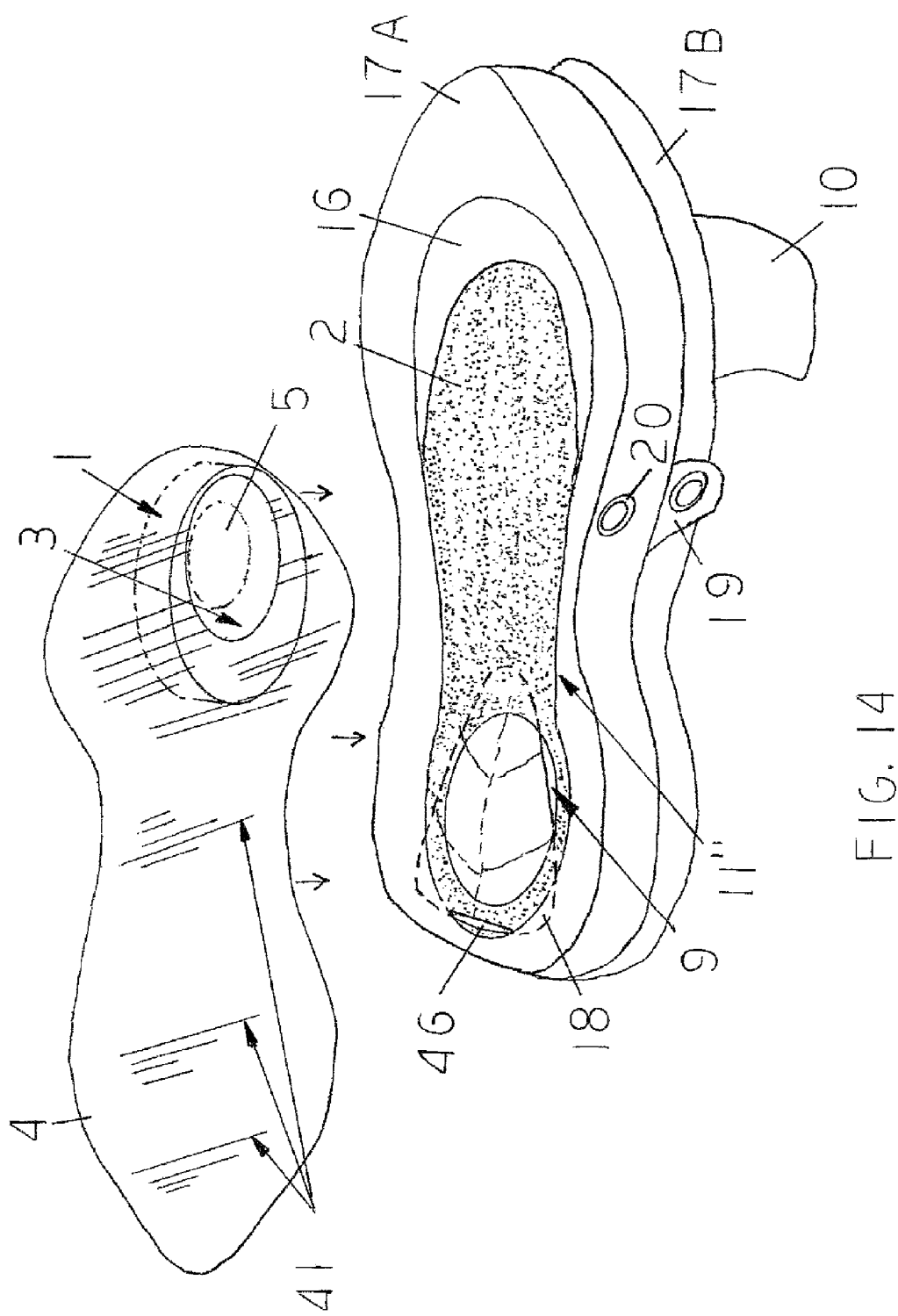
FIG. 14 is a partially exploded perspective view from the top of the third preferred embodiment of the present invention that includes the absorbent insert extension shown in FIG. 13 and the bandage with connected absorbent insert ring component that is shown in FIG. 12, both being used with a two-part stool collection bag having a bottom drain and a stool slider that is shown positioned within a top collection bag opening having remote positioning to the collection bag's drain.
Figure 15:
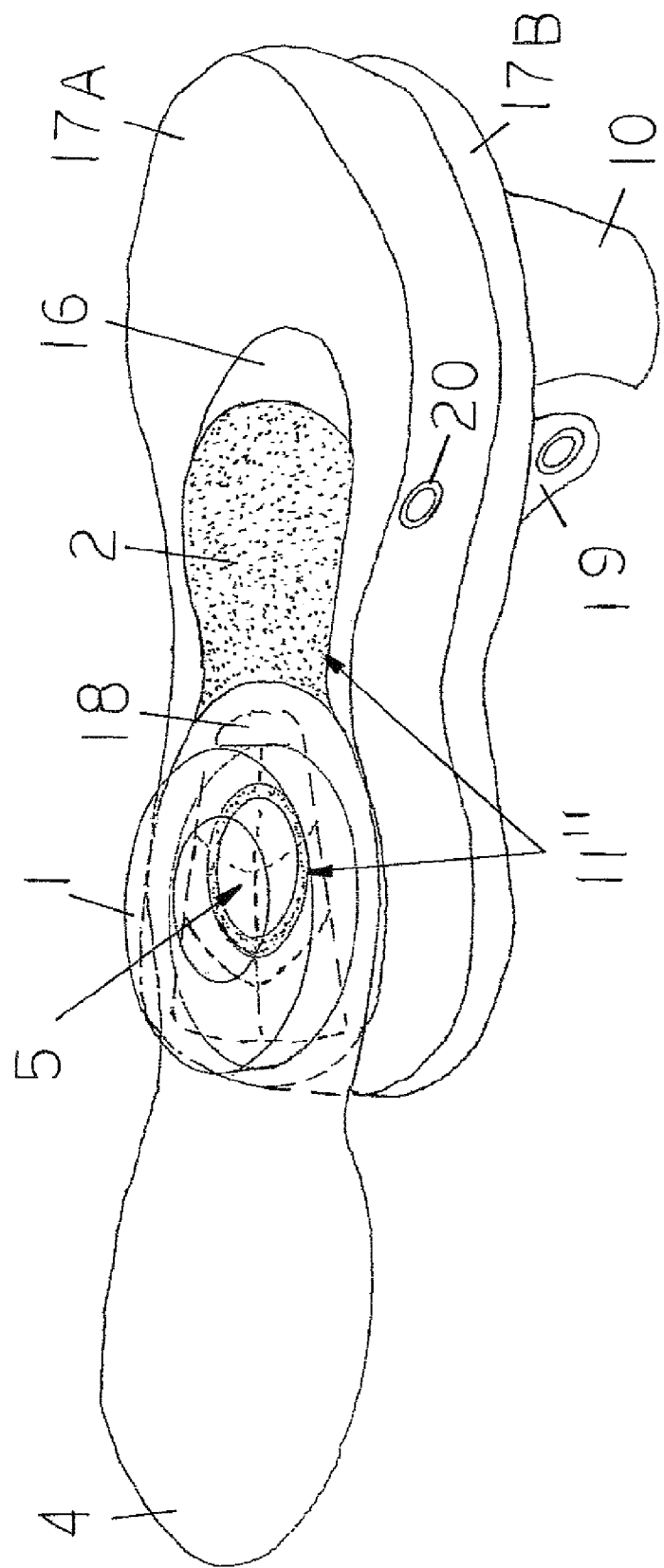
FIG. 15 is a side view from the top of the third preferred embodiment of the present invention previously shown in FIG. 14 and all components in their preferred positions of use.

FIGS. 12-15 disclose a third preferred embodiment of the present invention anti-channeling stool management system. FIG. 12 is a perspective view of absorbent insert ring component 1 associated with an elongated bandage 4 used to assist in securing ring component 1 into its desired position of use. FIG. 13 is a top view of an elongated absorbent insert extension 11" having an aperture 15 near one of its ends and a core 2 made from absorbent material, such as SAP, that can be used as a part of the third preferred embodiment of the present invention, with the absorbent exterior layer 16 of elongated absorbent insert extension 11" only partially shown to reveal the presence of the SAP material throughout the interior instead of using the elongated projections 12 shown in FIGS. 8 and 11. FIG. 14 is a partially exploded perspective view from the top of the third preferred embodiment of the present invention that includes the absorbent insert extension 11" shown in. FIG. 13 and the elongated bandage 4 with connected absorbent insert ring component 1 that is shown in FIG. 12, and both being used with a two-part stool collection bag (17A and 17B) having a bottom drain 10 and a stool slide 18 that is shown partially positioned under a top collection bag opening 9 having remote positioning to bottom drain 10. It is intended for the positioning of stool slide 18 to be fixed into a downwardly-slanting angled orientation relative to bag opening 9, and for a small amount of adhesive material 46 (or other bonding material) to connect stool slide 18 inside top bag member 17A to a portion of its inside top surface adjacent to bag opening 9. It is also contemplated for stool slide 18 to have a smooth and/or otherwise slippery surface that facilitates stool transfer to a stool collection bag (such as but not limited to 17A). Furthermore, lines 41 in FIG. 14 indicate the bottom non-adhesive surface of bandage 4 and FIG. 14 also shows the non-centered bore 3 through ring component 1. In addition FIG. 14 shows a snap 20 on top bag member 17A in close association with a complementary wing/snap 19 that are used together to pull bottom bag member 17B up and open to prevent complete collapse of bottom bag member 17B so that moisture and soft stool (not shown) can be continuously flow into bottom bag member 17B. FIG. 15 is a side view from the top of the third preferred embodiment of the present invention previously shown in FIG. 14 and all components in their preferred positions of use, except that wing/snap 19 is not yet connected to snap 20. For clarity of illustration in FIG. 15, a line was not used to identify bag opening 9 and the adhesive material 46 was also omitted.

Figure 16:
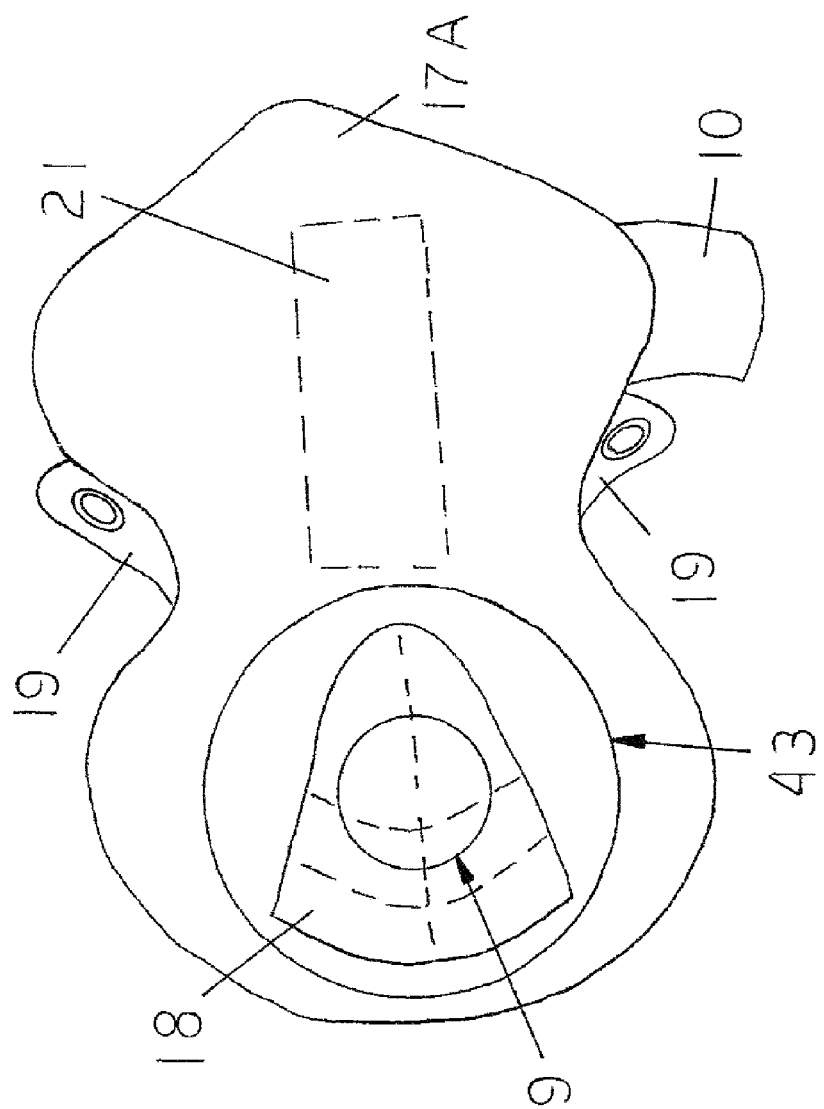
FIG. 16 is a top view of a preferred embodiment of a two-part stool collection bag that is usable as a part of a fourth preferred embodiment of the anti-channeling stool management system of the present invention, with the bag having a shortened length dimension and the hook/rough portion of a hook-and-loop fastener secured to the bag to assist in securing it to a user's undergarment or diaper, with FIG. 16 also showing a stool slide used with the top bag member and the wing/snap connectors used to fasten the top and bottom bag members together and prevent full collapse of the bottom bag so that stool collected in the top bag member can move via gravity into the bottom bag member where it can be maintained further away from a patient's skin and periodically removed through a bottom drain.

FIG. 16 discloses a fourth preferred embodiment of the present invention anti-channeling stool management system configured for male patient 27B use since the bag opening 9 is not closer toward the end of stool collection bag (17A and 17B) remote from drain 10 so that the vaginal area 28 of a female patient 27A does not become blocked by stool collection bag (17A and 17B). FIG. 16 is a top view of a preferred embodiment of a two-part stool collection bag (17A and 17B) that has a shortened length dimension and the rough/hook portion 21 of a hook-and-loop fastener that is shown in broken lines to indicate a secured position against the bottom surface of bottom bag member 17B. Rough/hook portion 21 assists in securing two-part stool collection bag (17A and 17B) to a male user's undergarment 33 (see FIG. 26) or diaper (not shown), with FIG. 16 also showing a stool slide used under the bag opening 9 of top bag member 17A to facilitate movement of moisture and soft stool away from bag opening 9. In addition, FIG. 16 shows the wing/snap connectors 19 used with snaps 20 to fasten the top and bottom bag members 17A and 17B together and in order to prevent full collapse of the bottom bag 17B so that stool collected in the top bag member 17A can move via gravity into the bottom bag member 17B where it can be removed through drain 10.

Figure 17:
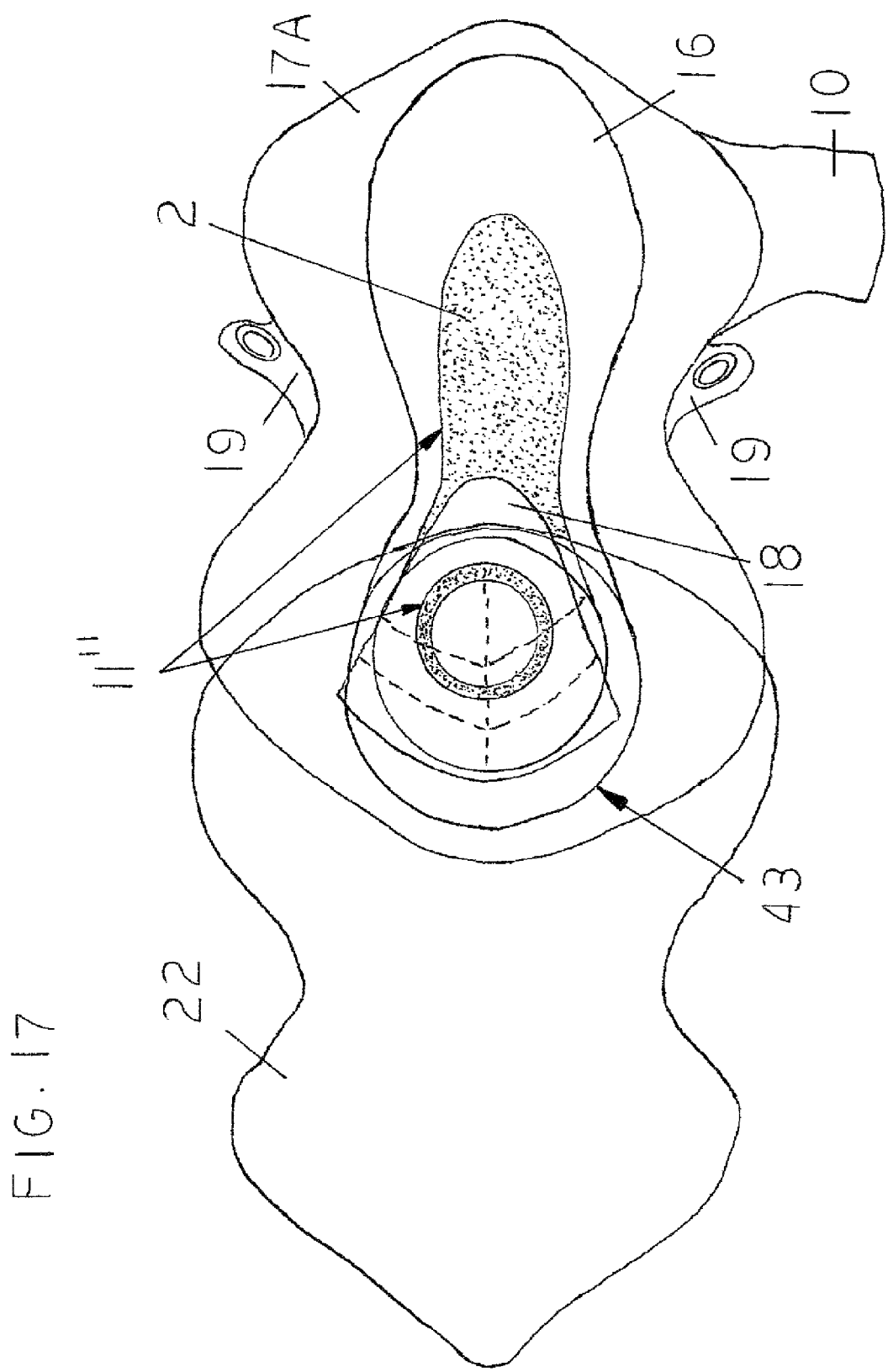
FIG. 17 is a top view of a fifth preferred embodiment of the present invention that uses the two-part stool collection bag shown in FIG. 16 and a broad butterfly-shaped bandage used to securely fix the present invention to a patient, with the broad butterfly-shaped bandage being much larger than the elongated bandage shown in FIGS. 12, 14, and 15 for a more secure hold.
Figure 18:
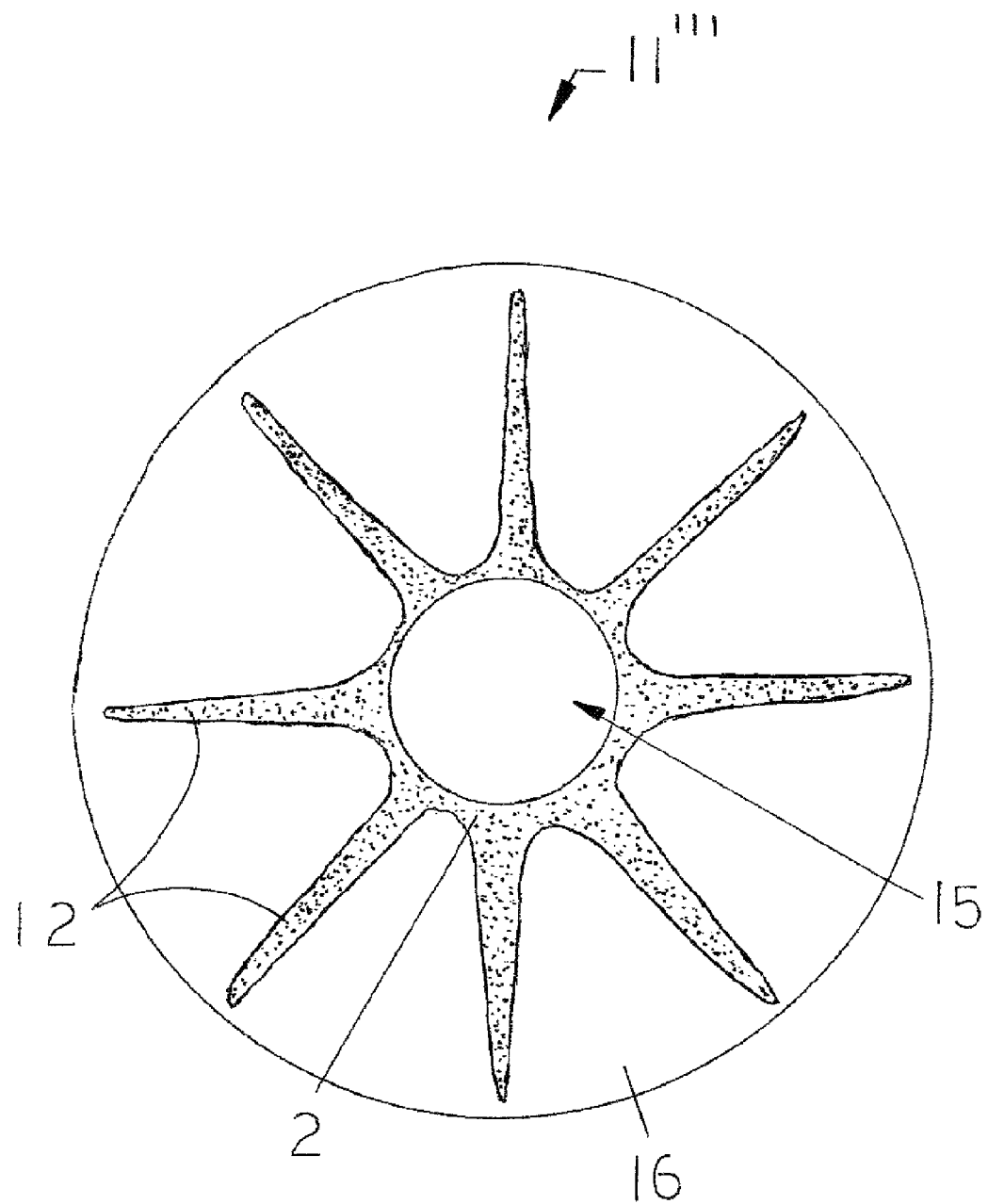
FIG. 18 is a sectional view of a large absorbent insert extension having a circular perimeter and multiple radially-extending projections of absorbent SAP material encased within an absorbent exterior layer/cover that is placed in fluid communication with an absorbent insert ring component when used as a part of the fifth preferred embodiment of the present invention to assist in drawing moisture away from a patient's skin.
Figure 19:
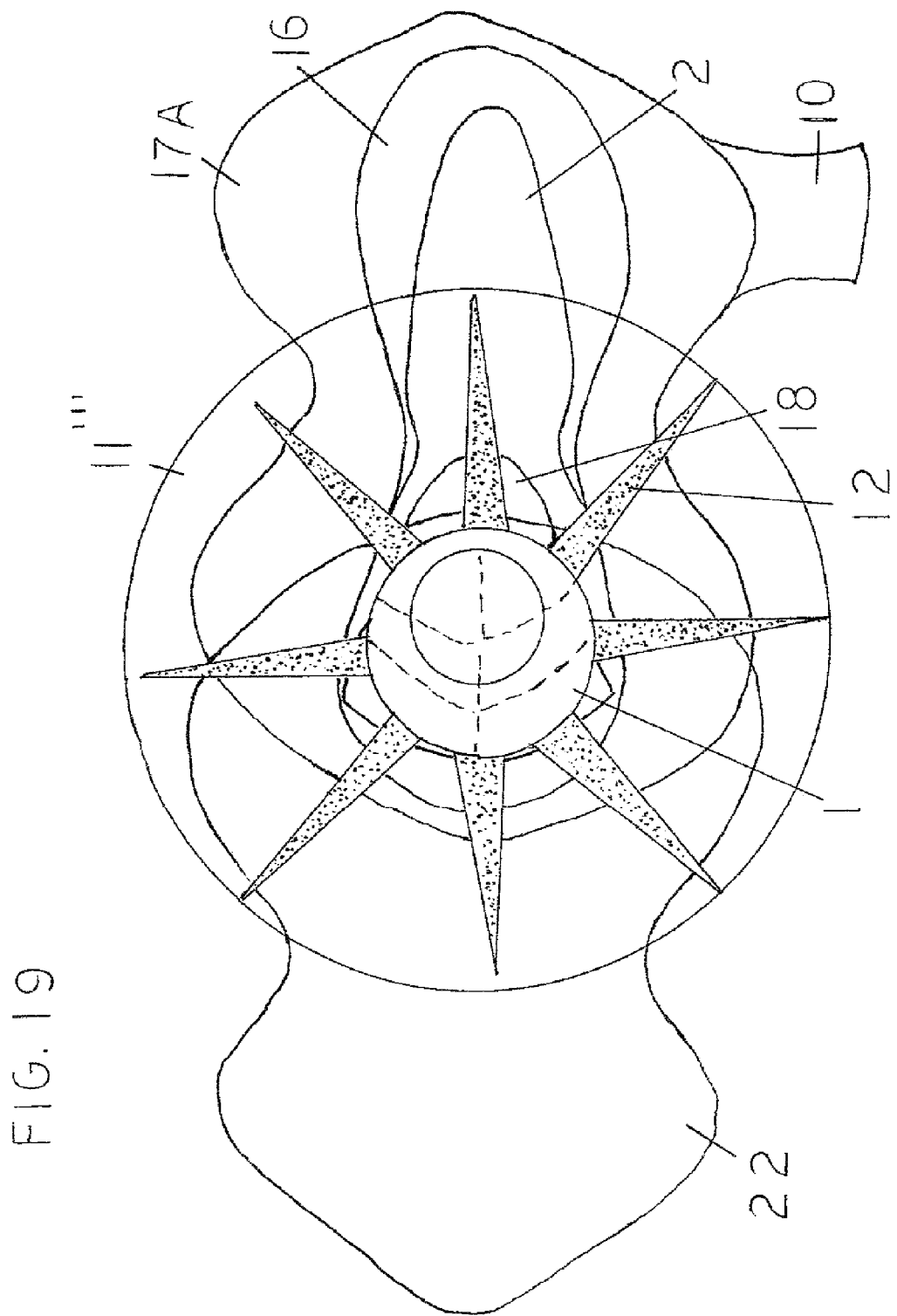
FIG. 19 is a top view of the large absorbent insert extension shown in FIG. 18 secured into its desired position of use as a part of the fifth preferred embodiment of the present invention.

FIGS. 17-19 disclose a fifth preferred embodiment of the present invention anti-channeling stool management system. FIG. 17 is a top view of a fifth preferred embodiment of the present invention that uses the two-part stool collection bag shown (17A and 17B) in FIG. 16 and a broad butterfly-shaped bandage 22 used to securely fix the present invention to a patient 27 that is larger than the elongated bandage 4 shown in FIGS. 12, 14, and 15. FIG. 17 also shows the absorbent insert extension 11" (previously shown in FIG. 13) and stool slide 18 connected to bag 17A. As mentioned before, absorbent exterior covering 16 is not shown fully around absorbent core 2 so that one can view its location, however, during use of absorbent insert extension 11" it is contemplated that covering 16 would completely encase core 2 so that no skin contact with SAP material will occur. FIG. 18 is a sectional view of a large absorbent insert extension 11' having a circular perimeter and multiple radially-extending projections 12 of absorbent SAP material encased within an absorbent exterior covering 16 that is placed in fluid communication with an absorbent insert ring component 1 when used as a part of the fifth preferred embodiment of the present invention to assist in drawing moisture and soft stool away from a patient's skin. FIG. 19 is a top view of the large absorbent insert extension 11' shown in FIG. 18 secured into its desired position of use as a part of the fifth preferred embodiment of the present invention, wherein the fifth preferred embodiment now has two absorbent insert extensions 11''' and 11" (shown in FIG.

19 by the numbers 2 and 16). Although core 2 in absorbent insert extension 11" has speckled shading in other illustrations herein to indicate SAP material, such shading was omitted in FIG. 19 only for clarity of illustration.

FIG. 20 is a perspective view from the side of two-part stool collection bag 17A and 17B usable as a part of various preferred embodiments of the present invention, with the bottom bag member 17B having snap/wing connectors 19, sufficient small beads 23 in the bottom bag member 17B to maintain an open configuration therein for stool collection, and fluid communication means 24 from the upper bag member 17A downward into lower bag member 17B via gravity, with fluid communication means 24 preferably comprising multiple one-way valves. Although FIG. 20 shows six one-way valves 24, the present invention is not limited to six individual sources of fluid communication 24, and more or less than six could be present. FIG. 20 also shows a strip of rough/hook portion 21 that assists in securing two-part stool collection bag (17A and 17B) to a user's undergarment 33 (see FIG. 26) or diaper (not shown). Stool slide 18 is also shown in its preferred position of use relative to top bag member 17A, and FIG. 20 further shows bag opening 9 having a larger spaced-apart distance from the end of top bag member 17A that indicates use by a male patient 27B, as the top bag member 17 shown in FIG. 20 could be at risk for blocking the vaginal area 28 of a female patient, which is not desired. FIG. 20 also shows optional deodorizer means 51 in top bag member 17A. It should be understood that the size, number, configuration, and location of the tablet shown as deodorizer means 51 are only representative and may be different from that shown, and in addition the deodorizer means 51 used may also be in liquid form in either (or both) stool collection bags 17A and 17B.

FIG. 21 is a perspective view of sixth preferred embodiment of the present invention absorbent insert in combination with an absorbent insert extension comprising core 2 and covering 16, and an elongated bandage 4 that would assist in securing ring component 1 in its desired position of use relative to a patient's rectal opening 8. FIG. 21 shows absorbent insert ring component 1 having a downwardly tapering central bore 25 and the end of bandage 4 remote from ring component 1 having a Y-shaped fastener 26 made from the soft/loop portion of a hook-and-loop fastener (or adhesive material). It is contemplated that Y-shaped fastener 26 would be connected on its distal end to a portion of rough/hook fastener or two-sided adhesive secured to a patient's back, such as that shown in FIG. 23 and marked by the number 21. As mentioned before, it is contemplated for absorbent exterior covering 16 to completely encase absorbent core 2 so that no skin contact with SAP material will occur, even though both remain visible in FIG. 21 for illustrative purposes.

FIGS. 22 and 23 disclose a seventh preferred embodiment of the present invention anti-channeling stool management system. FIG. 22 is a top view of an arcuate bandage 29, with the visible portion of arcuate bandage 29 extending across the center part of the crotch area of a female patient between the rectal opening 8 and the vaginal area 28. FIG. 22 also shows arcuate bandage 29 further extending onto both sides of the buttocks area of the female patient 27A. FIG. 23 is a rear view of the seventh preferred embodiment of the present invention which has the arcuate bandage 29 extending from the center part of the crotch area of a female patient 27A and then upwardly onto the patient's buttocks, and a generally butterfly-shaped bandage 22 having an attached absorbent insert ring component 1 aligned with the rectal opening 8 of the patient (for clarity of illustration rectal opening 8 is not visible in FIG. 23). FIG. 23 also shows bandage 22 extending upwardly across the back of patient 27A for secure connection to patient 27A outside the zone 30 of potential stool influence that is likely to experience skin breakdown should stool leakage occur for any reason. In addition, FIG. 23 shows the distal end of bandage 22 connected to two soft/loop portions of hook-and-loop fastener 31 (could also be an adhesive), which are placed in contact with the rough/hook portion of a hook-and-loop fastener 21 (could also be adhesive or double-sided adhesive). In addition, FIG. 23 shows the break-away portion 49 of arcuate bandage 29, which could be larger or smaller than is shown in FIG. 23, with break-away portion 49 potentially allowing continued use of the present invention while skin breakdown centrally on patient 27A (that would otherwise be under part of all of break-away portion 49) is allowed to heal.

FIG. 24 is a rear view of a male patient 27B showing that it is intended for preferred embodiments of the present invention to be positioned for use in approximately the same area where an incontinence pad would be used, the vertical orientation of the illustration in FIG. 24 being selected to provide better understanding of the intended positioning without implying that the patient is ambulatory. FIG. 24 shows a present invention ring component 1 aligned with a rectal opening 8, and a bandage 4 secured to the back of patient 27B. In addition, FIG. 23 shows a single stool collection bag 32 also in fluid communication with ring component 1, and bag 32 having a drain for periodically evacuating stool and urine therefrom. Bag 32 has a top surface that wicks urine downwardly away from patient skin.

FIGS. 25 and 26 disclose an eighth preferred embodiment of the present invention anti-channeling stool management system. FIG. 25 is a top view of an eighth preferred embodiment contemplated for use on a male patient for stool and urine collection, with ring component 1 secured into its position of use in alignment with the rectal opening 8 of a patient 27B, and an adhesive bandage 4 extending rearwardly from rectal opening 8 for attachment to the backside of a patient. FIG. 25 also shows a stool and urine bag 32 extending forwardly from rectal opening 8, with a rough/hook portion 21 of a hook-and-loop fastener attached to the bottom surface of stool collection bag 32 that securely fixes collection bag 32 to an adjacent part of an undergarment 33 worn by male patient 27B. FIG. 26 is a perspective view of the eighth preferred embodiment of the present invention and shows ring component 1, bandage 4, bag 32, and rough/hook portion 21 in their intended positions of use.

Figure 27:
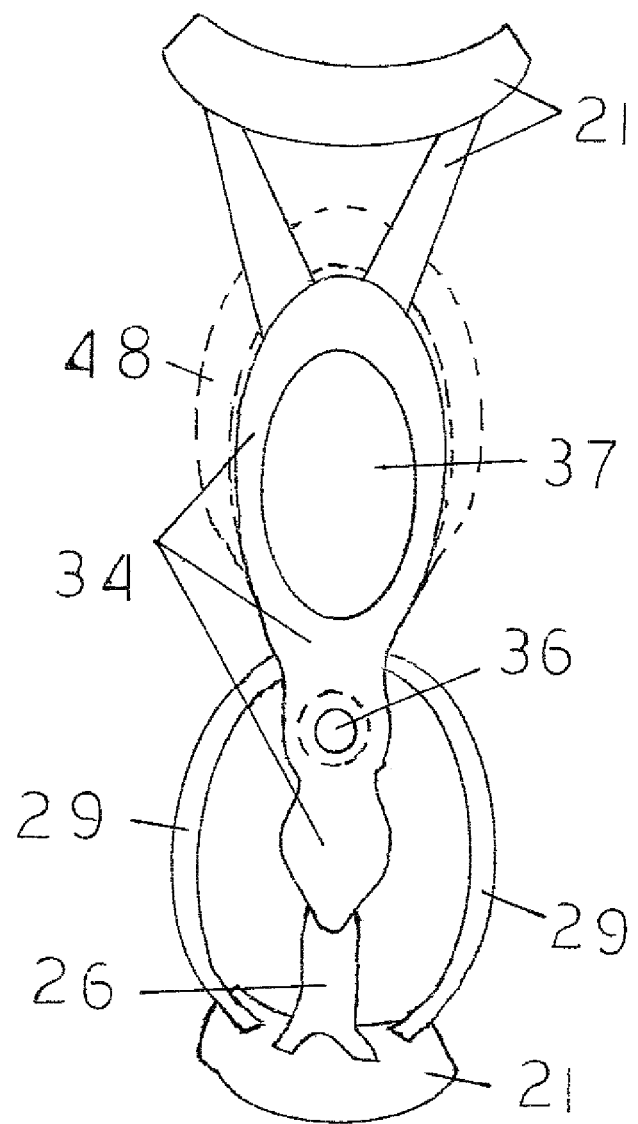
FIG. 27 is a bottom view of a ninth preferred embodiment of the present invention intended for use on a female patient and having an arcuate bandage configured for positioning from the center part of the crotch area of the female patient and then upwardly across the patient's buttocks, and the arcuate bandage attached to a triangular-shaped rear receiving fastener fixed on the patient's back to skin outside the zone of potential stool influence (shown by the number 30 in FIG. 23), with FIG. 27 also showing a sling having a urine transfer opening, front and back fasteners that attach to the patient, and a stool transfer opening that is aligned with the bore of an attached absorbent insert ring component, with both the stool transfer opening and the bore of ring component positioned for alignment with the rectal opening of a female patient without blocking the urine transfer opening.
Figure 28:
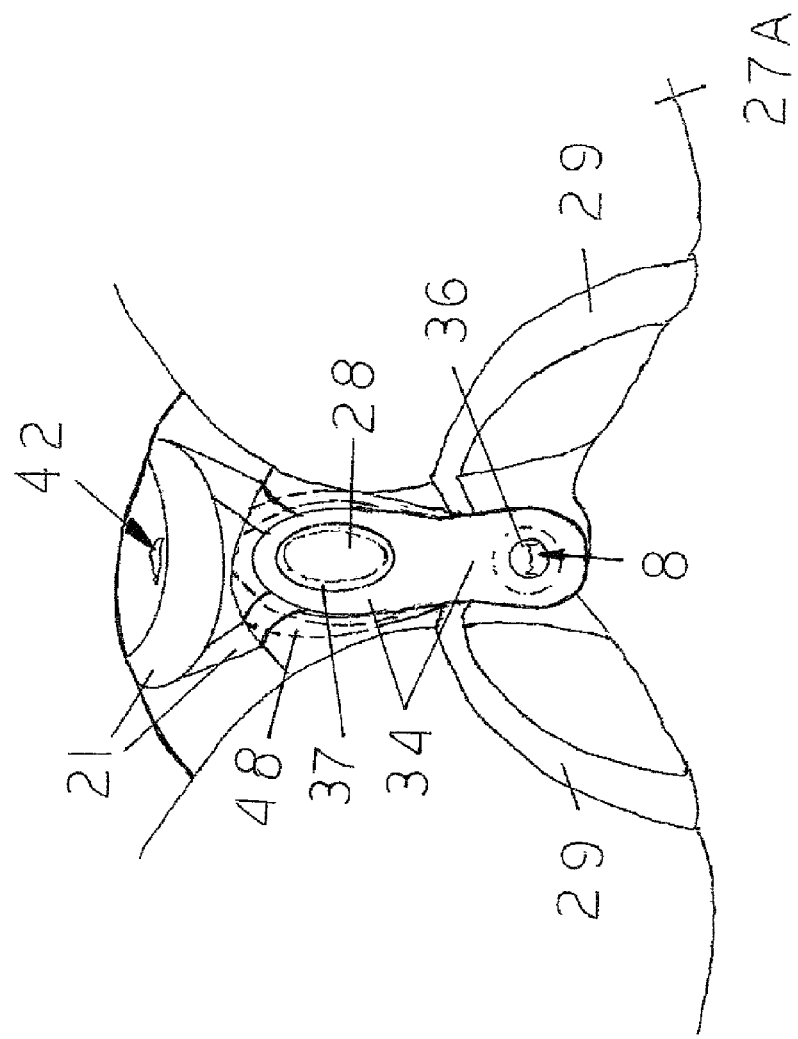
FIG. 28 is a bottom view of the ninth preferred embodiment of the present invention in its intended position of use with the generally triangular-shaped single or multiple piece fastener that becomes fixed to the front of the female patient shown secured under the patient's naval.
Figure 29:
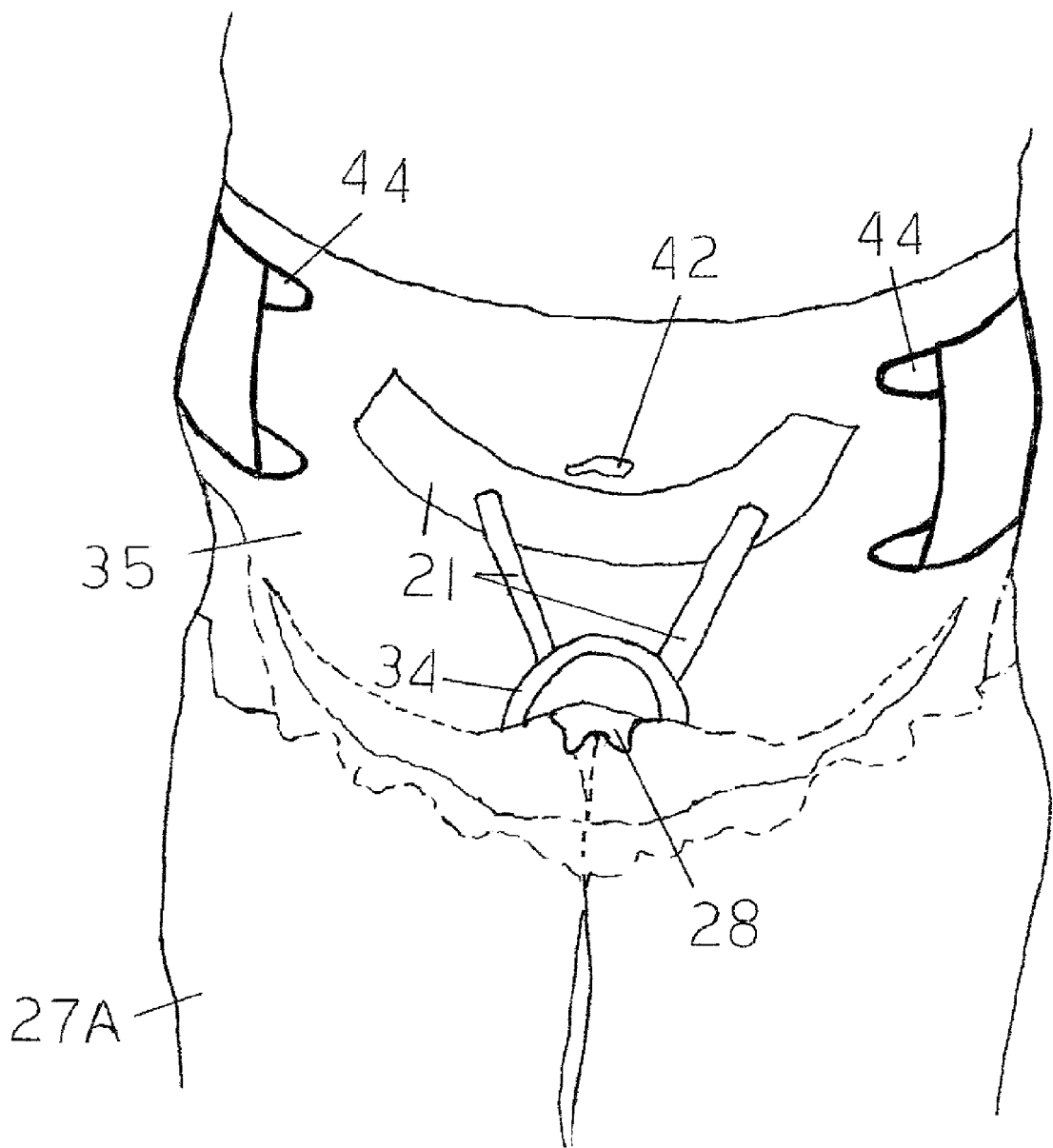
FIG. 29 is a front view of the ninth preferred embodiment of the present invention secured to a female patient and the patient wearing a diaper over the present invention, with a seal of one-way wicking material in the portion of the diaper adjacent to the patient's skin causing the diaper to become a collection bag for stool and urine that prevents adverse affects of stool or urine on the patient's skin.

FIG. 27 is a bottom view of a ninth preferred embodiment of the present invention intended for use on a female patient 27A and having an arcuate bandage 29 extending from the center part of the crotch area of female patient 27A and then upwardly across the patient's buttocks, with arcuate bandage 29 being sufficiently long to attach to a triangular-shaped rear receiving fastener 21 fixed on the patient's back to skin outside the zone of potential stool influence (shown by the number 30 in FIG. 23) should stool leakage. FIG. 27 also shows a sling 34 having a urine transfer opening 37 and a stool transfer opening 36 that is aligned with the bore 2 of an attached absorbent insert ring component 1, with both stool transfer opening 36 and the bore 2 of ring component 1 positioned for alignment with the rectal opening 8 of the female patient 27A (which for clarity of illustration is not shown in FIG. 27). In addition, the ninth preferred embodiment of the present invention also has a Y-shaped fastener 26 secured to the end of sling 34 adjacent to ring component 1 wherein the distal end of the Y-shaped fastener 26 can become secured to the same receiving fastener 21 having a connection to the arcuate bandage or bandages 29 (two arcuate bandages 29 would be present if the break-away portion 49 shown in FIG. 23 is removed). FIG. 27 further shows urine transfer opening 37 aligned with a reinforced edge 48 around a similar urine transfer opening 37 in a diaper (see FIG. 30) and a generally triangular-shaped single or multiple piece fastener 21 that becomes fixed to the front of a female patient 27A to secure the ninth preferred embodiment in its desired position of use independent of any underwear 33, incontinence pad (not shown), or diaper (35 or other). As shown in FIG. 28, generally triangular-shaped fastener 21 is typically secured under the navel 42 of a female patient 27A. FIG. 28 is a bottom view of the ninth preferred embodiment of the present invention in its intended position of use with the generally triangular-shaped single or multiple piece fastener 21 that becomes fixed to the front of a female patient 27A shown secured under the patient's naval 42. Ring component 1 is illustrated in broken lines, as it is positioned under sling 34 against patient skin around the rectal opening 8. As points of reference, the reinforced edge 48 around a urine transfer opening 37 in a diaper 35 (see FIG. 30) is also shown around one end of sling 34, and the vaginal area 28 of female patient 27A is also marked. The arcuate bandages 29 are also shown in FIG. 28 secured to female patient 27A between the rectal opening 8 and the vaginal area 28, and the number 36 is used to identify the stool transfer opening in sling 34. FIG. 29 is a front view of the ninth preferred embodiment of the present invention secured to a female patient 27A and patient 27A wearing a diaper 35 over the ninth preferred embodiment, with the one-way wicking material 6 (see FIG. 30) in the portion of diaper 35 adjacent to the patient's skin allowing diaper 35 to become a collection bag for stool and urine that prevents adverse affects of skin or urine on the patient's skin. Sling 34 may be made from plastic material, but is not limited thereto.

Figure 30:
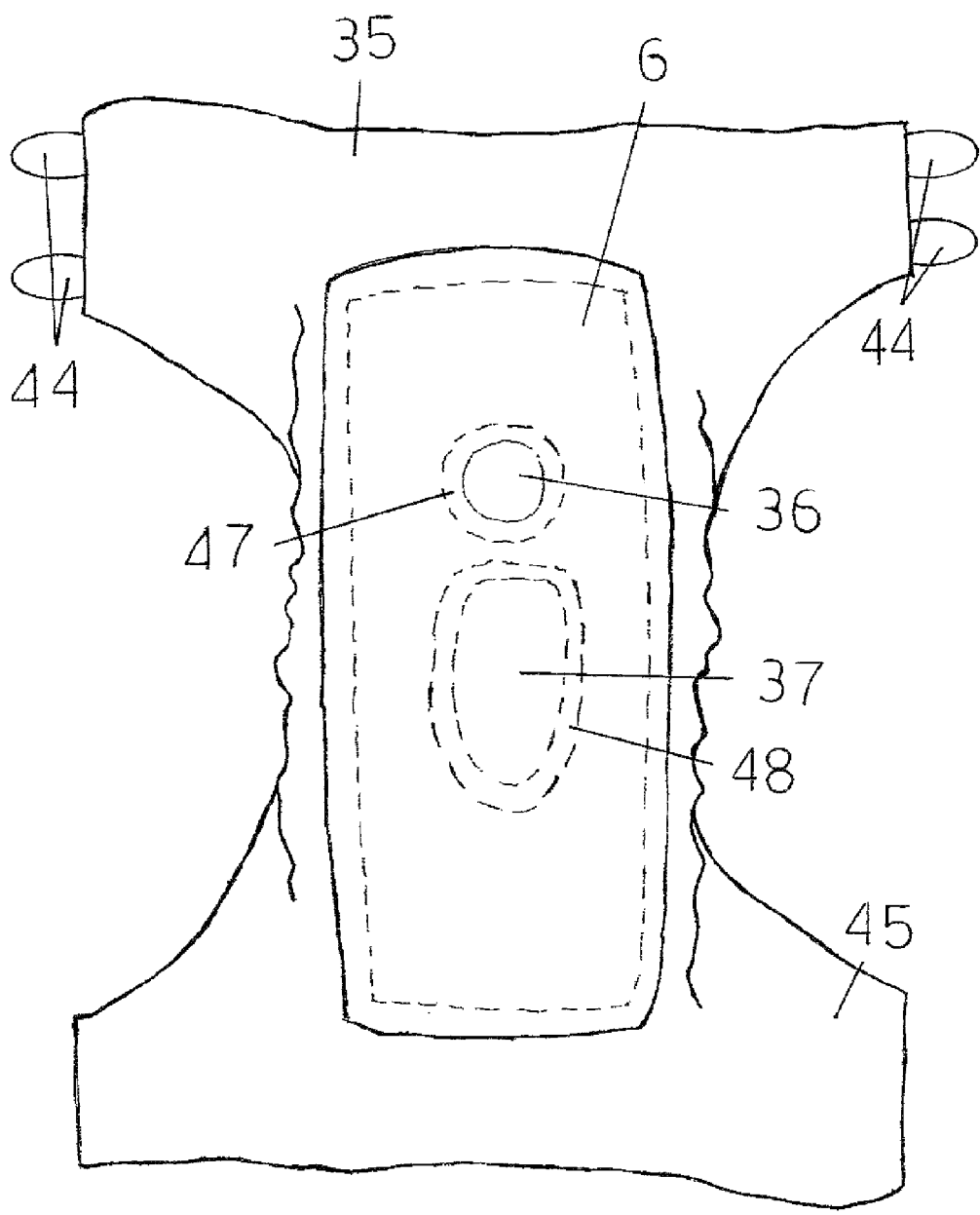
FIG. 30 is a perspective view of a preferred diaper that could become a part of the ninth preferred embodiment of the present invention, and the two openings therein that are intended to align with the bore of the ring component for stool transfer into the diaper and the urine opening aligned with the vaginal area of the female patient.
Figure 31:
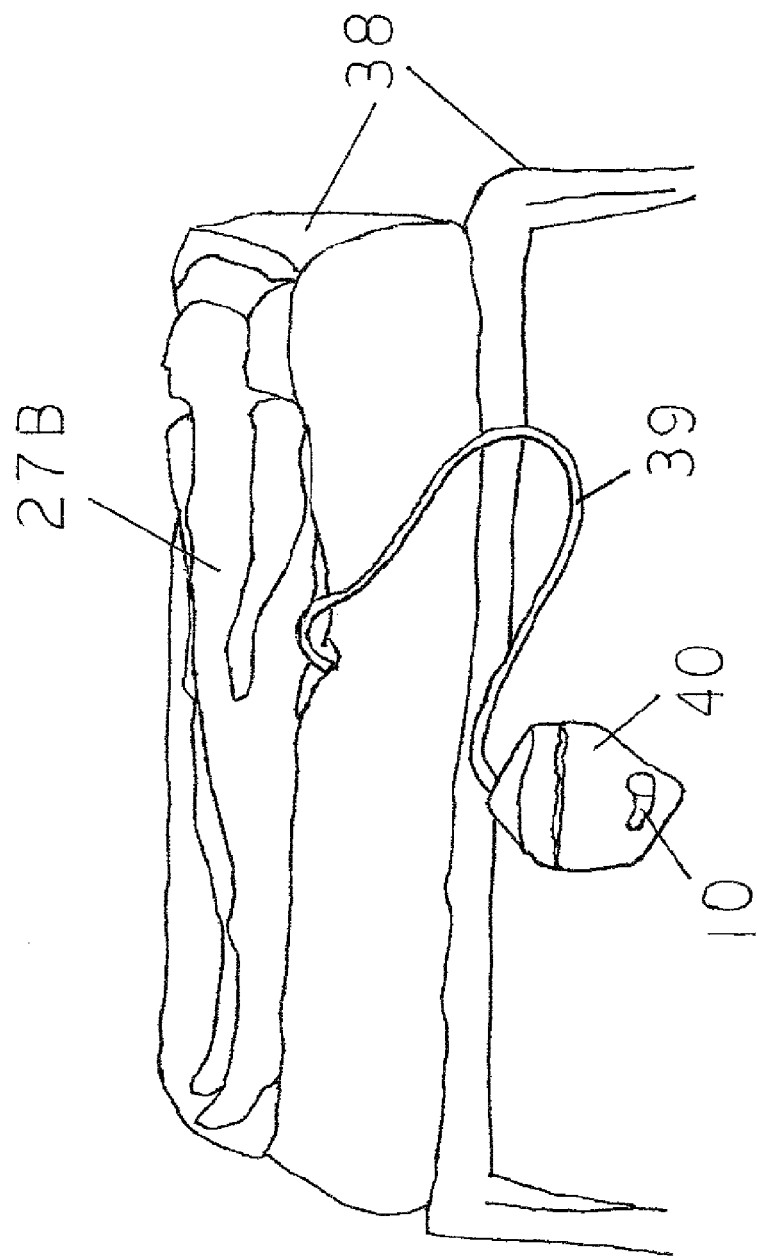
FIG. 31 is a side view of a patient in bed that shows tubing extending from a position beneath the patient to a Foley catheter bag suspended from the side of the bed, with the stool collection bag of a preferred embodiment of the present invention anti-channeling stool management system connected out-of-view to the hidden end of the tubing, wherein the drain on the Foley catheter bag allows removal of collected stool therefrom without any disturbance affecting the present invention collection system.

FIG. 30 is a perspective view of a preferred diaper 35 that could become a part of the ninth preferred embodiment of the present invention, and the two openings (36 and 37) therein, stool transfer opening 36 that is intended to align with the bore 3 of the ring component 1 for stool transfer into diaper 35 and the urine opening 37 that is aligned with the vaginal area 28 of the female patient 27A. FIG. 30 also shows wings 45 and fastening tabs 44 that are used to enwrap diaper 35 around female patient 27A. FIG. 30 further shows the seal 6 turns diaper 35 into a collection bag. It is contemplated for seal 6 to have other sizes and configurations from that shown in FIG. 30.

FIG. 31 is a side view of a male patient 27B in bed 38 that shows tubing 39 extending from a position beneath patient 27B to a Foley catheter bag 40 suspended from the side of bed 38, with the stool collection bag (not shown in FIG. 31, as it is beneath patient 27B) of a preferred embodiment of the present invention anti-channeling stool management system connected out-of-view to the hidden end of tubing 39, wherein the drain 10 on the Foley catheter bag 40 allows removal of collected stool (not shown) therefrom without any disturbance affecting the present invention collection system.

While the written description of the invention herein is intended to enable one of ordinary skill to make and use its best mode, it should also be appreciated that the invention disclosure only provides examples of specific embodiments and methods, and many variations, combinations, and equivalents also exist which are not specifically mentioned. The present invention should therefore not be considered as limited to the above-described embodiments, methods, and examples, or the language in the accompanying Abstract, but instead encompassing all embodiments and methods within the scope and spirit of the invention.

I claim:

1. A stool management and collection system for acutely and chronically ill patients that directs substantially all stool into a collection container and prevents channeling of stool onto patient skin which can quickly lead to the breakdown of patient skin, patient discomfort, and the spread of disease, said system comprising:
    a bandage attached to patient skin in a fixed position around the rectal opening, said bandage having a hole through which the rectal opening is exposed;
    an absorbent insert ring component secured to said bandage and having a bore with a waterproof interior that when aligned with a rectal opening directs stool released by the rectal opening through said waterproof interior of said bore, said ring component also having an inner core and an outer covering made from absorbent material that completely encases said inner core and is in fluid communication with said inner core, said outer covering positioned to absorb moisture and soft stool channeling between said bandage and patient skin around the rectal opening, said inner core made from super absorbent material that draws and traps moisture and soft stool first absorbed by said outer covering, drawing and keeping it away from the rectal opening and patient skin; and
    a water-resistant seal extending across any space between said ring component and said hole in said bandage when said bore of said ring component is aligned with a rectal opening for stool transfer use, wherein when said bore in said insert ring component is aligned with an opening in a stool collection container with said waterproof interior directing substantially all stool into the collection container, moisture and soft stool attempting to channel under said bandage instead becomes trapped in said inner core after first passing through said outer covering, preventing the channeling of stool under said bandage and onto patient skin, and reducing opportunity for skin breakdown and spread of disease.

2. The system of claim 1 wherein said inner core is capable of absorbing approximately forty to sixty times its weight in fluid.

3. The system of claim 1 wherein said inner core comprises super absorbent polymer.

4. The system of claim 1 further comprising an absorbent insert extension in fluid communication with said ring component.

5. The system of claim 1 wherein said absorbent insert extension comprises a core of absorbent material capable of absorbing more than forty times its weight in fluid and an outer covering made from absorbent material that completely encases said inner core.

6. The system of claim 5 comprising two of said absorbent insert extensions.

7. The system of claim 4 wherein a core of said absorbent insert extension comprises a super absorbent polymer.

8. The system of claim 4 wherein a core of said absorbent insert extension further comprises components selected from a group consisting of said core made from super absorbent polymer, a plurality of elongated projections made from super absorbent polymer extending outwardly from said core, and said outer covering having expansion folds.

9. The system of claim 1 for a female patient wherein said bandage is elongated with opposing ends and a hole therethrough close to one of said opposing ends at a spaced-apart distance that allows said ring component to be aligned with said hole and the rectal opening of the patient without any portion of said bandage blocking the vaginal area of the patient.

10. The system of claim 9 wherein said bore in said ring component is non-centered in a manner that prevents any blocking of the vaginal area of the patient when it is aligned with said hole in said bandage.

11. The system of claim 1 further comprising a fecal collection bag with a bag opening configured for alignment with said bore in said ring component, and fastening means to secure said fecal collection bag in approximately the same area where an incontinence pad is normally positioned.

12. The system of claim 11 further comprising a downwardly angled slide connected to said fecal collection bag with an orientation that facilitates movement by gravity of moisture and soft stool into said fecal collection bag.

13. The system of claim 11 wherein said fecal collection bag further comprises two part construction having a top bag member and a bottom bag member and a drain, and features selected from a group consisting of at least one snap connected to one of said bag members and a complementary wing and snap combination connected to the other of said bag members for securing said top and bottom bag members together and pulling up and preventing collapse of said bottom bag member, soft small beads positioned within said bottom bag member to further prevent collapse of said bottom bag member, deodorizer means in at least one of said bag members, and fluid communication means between said top and bottom bag members.

14. The system of claim 1 wherein said bore of said ring component has a tapering configuration.

15. The system of claim 1 further comprising a receiving fastener secured to a patient and at least one additional fastener connected between said receiving fastener and said bandage.

16. The system of claim 1 further comprising at least one arcuate bandage configured for extending from the skin of a female patient between the rectal opening and the vaginal area, and then extending up onto the buttocks of the patient.

17. The system of claim 16 wherein said at least one arcuate bandage is further configured with a break-away portion.

18. The system of claim 1 having a single urine and stool collection bag in fluid communication with said ring component for male patients.

19. The system of claim 1 wherein said bandage comprises the configuration of a sling for female patients, said sling having a stool transfer opening and a urine transfer opening.

20. The system of claim 19 further comprising a diaper with a first reinforced edge around a stool transfer opening that is configured to align with said stool transfer opening in said sling, and a second reinforced edge around a urine transfer opening that is configured to align with said urine transfer opening in said sling.

* * * * *